(12) United States Patent
Giaffreda et al.

(10) Patent No.: US 10,946,027 B2
(45) Date of Patent: *Mar. 16, 2021

(54) TIANEPTINE OXALATE SALTS AND POLYMORPHS

(71) Applicant: Tonix Pharma Holdings Limited, Hamilton (BM)

(72) Inventors: Stefano Luca Giaffreda, Bologna (IT); Enrico Modena, Bologna (IT); Serena Fabbroni, Medicina (IT); Michel Chiarucci, Bologna (IT); Mark T. Edgar, Rancho Santa Fe, CA (US)

(73) Assignee: Tonix Pharma Holdings Limited, Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 16/597,065

(22) Filed: Oct. 9, 2019

(65) Prior Publication Data

US 2020/0276208 A1    Sep. 3, 2020

Related U.S. Application Data

(63) Continuation of application No. 15/856,818, filed on Dec. 28, 2017, now Pat. No. 10,449,203.

(60) Provisional application No. 62/439,533, filed on Dec. 28, 2016.

(51) Int. Cl.
*A61K 31/554* (2006.01)
*A61P 25/24* (2006.01)
*C07D 281/02* (2006.01)

(52) U.S. Cl.
CPC .......... *A61K 31/554* (2013.01); *C07D 281/02* (2013.01); *A61P 25/24* (2018.01)

(58) Field of Classification Search
CPC .............................. A61K 31/554; A61P 25/24
See application file for complete search history.

(56) References Cited

U.S. PATENT DOCUMENTS

| | | | |
|---|---|---|---|
| 5,405,842 A | 4/1995 | Silverman | |
| 6,599,896 B1 | 7/2003 | Deslandes | |
| 8,198,268 B2 | 6/2012 | Guzman | |
| 9,314,469 B2 | 4/2016 | Sullivan | |
| 10,449,203 B2 * | 10/2019 | Giaffreda | A61P 25/14 |
| 2007/0010502 A1 | 1/2007 | Keith | |
| 2009/0275541 A1 | 11/2009 | Sullivan | |
| 2010/0112051 A1 | 5/2010 | Guzman | |
| 2016/0256471 A1 | 3/2016 | Sullivan | |

FOREIGN PATENT DOCUMENTS

FR          2635461        2/1990
WO    WO2010051239        5/2010

OTHER PUBLICATIONS

Brink et al., "Tianeptine: a novel atypical antidepressant that may provide new insights into the biomolecular basis of depression," Recent Pat CNS Drug Discov, 1:29-41 (2006).
Conrad et al., "Chronic stress impairs rat spatial memory on the Y maze, and this effect is blocked by tianeptine pretreatment," Behav Neurosci, 110:1321-1334 (1996).
Czeh et al., "Stress-induced changes in cerebral metabolites, hippocampal volume, and cell proliferation are prevented by antidepressant treatment with tianeptine," Proc Natl Acad Sci USA 98:12796-12801 (2001).
File et al., "Effects of tianeptine in animal models of anxiety and on learning and memory," Drug Development Research, 23:47-56 (1991).
Hilfiker, "Polymorphism: in the Pharmaceutical Industry," pp. 1-19 (Jan. 1, 2006).
Jaffard et al., "Effects of tianeptine on spontaneous alternation, simple and concurrent spatial discrimination learning and on alcohol-induced alternation deficits in mice," Behav Pharmacol, 2:37-46 (1991).
Kumar et al., "Salt selection in drug development," Pharmaceutical Technology, 32(3):128-146 (2008).
McEwen et al., "Neurobiology of mood, anxiety, and emotions as revealed by studies of a unique antidepressant: tianeptine," Mol Psychiatry, 10:525-537 (2005).
Morris et al., "Tianeptine and its enantiomers: effects on spatial memory in rats with medial septum lesions," Neuropharmacology, 41:272-281 (2001).
Watanabe et al., "Tianeptine attenuates stress-induced morphological changes in the hippocampus," Eur J Pharmacol, 222:157-162 (1992).

(Continued)

*Primary Examiner* — Joseph R Kosack
(74) *Attorney, Agent, or Firm* — Haley Guiliano LLP; James F. Haley, Jr.

(57) ABSTRACT

Disclosed herein is an oxalate salt/co-crystal (tianeptine oxalate) of (RS)-7-(3-chloro-6-methyl-6,11-dihydrodibenzo [c,f] [1,2]thiazepin-11-ylamino)heptanoic acid S,S-dioxide (tianeptine) as shown in Formula I:

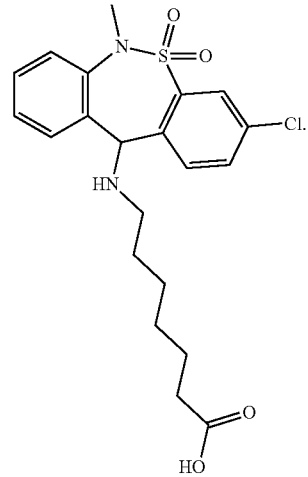

Formula I

21 Claims, 16 Drawing Sheets

(56) References Cited

OTHER PUBLICATIONS

Lechin et al., "The serotonin uptake-enhancing drug tianeptine suppresses asthmatic symptoms in children: a double-blind, crossover, placebo-controlled study," Journal of Clinical Pharmacology, 38:918-925 (1998).

Paulekuhn et al., "Trends in active pharmaceutical ingredient salt selection based on analysis of the Orange Book database," Journal of Medicinal Chemistry, 50(26):6665-6672 (2007).

* cited by examiner

TIANEPTINE OXALATE SALTS AND POLYMORPHS

CROSS-REFERENCE TO RELATED APPLICATIONS

This application is a continuation application of U.S. patent application Ser. No. 15/856,818, filed Dec. 28, 2017 (now allowed), which claims the benefit of and priority from U.S. Provisional Application 62/439,533, filed Dec. 28, 2016, the contents and disclosures of each of which are incorporated herein by reference in their entireties.

FIELD OF THE INVENTION

The present disclosure is in the field of salts/co-crystals of tianeptine, including polymorphic forms of tianeptine oxalate, methods of making the salts and polymorphic forms, and pharmaceutical compositions comprising them are also described.

BACKGROUND OF THE DISCLOSURE

Tianeptine, or 7-[(3-chloro-6-methyl-5,5-dioxo-11H-benzo[c][2,1]benzothiazepin-11-yl)amino]heptanoic acid, is an antidepressant with cognitive restorative effects. Investigators have reported that it can be used to treat post-traumatic stress disorder (PTSD) (Onder E. et al., (2005), *European Psychiatry* 21:174-179).

Although tianeptine shares structural similarities to classic tricyclic antidepressants, its pharmacological behavior is unique. More commonly known by the commercial names Stablon®, Coaxil, Tatinol, Tianeurax, and Salymbra, tianeptine is currently available throughout Europe, Asia, and Latin America for the treatment of depression. Tianeptine modulates the glutamatergic system and reverses the inhibitory neuroplasticity observed during periods of stress and steroid use. In modulating the glutamatergic system, tianeptine normalizes glutamate levels in the hippocampus, amygdala, and prefrontal cortex. Through genomic and non-genomic mechanisms, glutamate modulation restores plasticity, relieves inhibition of long-term potentiation, and reverses structural changes induced by chronic exposure to corticosteroids.

Tianeptine's anxiolytic properties and its reported ability to modulate the neuroendocrine stress response suggest that it can be used to treat PTSD. In fact, several studies have shown tianeptine to be an effective therapy for patients with PTSD because it is reported to improve many of the condition's characteristic symptoms (Crocq L & Goujon C: The Anxio-Depressive component of the psychotraumatic syndrome and its treatment by tianeptine. *Psychol Med*, 1994; 26 (2): 192-214; Rumyantseva G M & Stepanov A L: Post-traumatic stress disorder in different types of stress (clinical features and treatment). *Neurosci Behav Physiol*, 2008; 38:55-61; and Frančišković, Tanja, et al. "Tianeptine in the combined treatment of combat related posttraumatic stress disorder." *Psychiatria Danubina* 23(3) (2011): 257-263).

In addition to tianeptine's neuro-protective actions, including its ability to reverse the structural changes and inhibition of long term potentiation (LTP) caused by steroid exposure, it is reported to be potentially useful for treating neurocognitive dysfunction and similar side effects in patients treated with corticosteroids. Tianeptine's ability to restore cognitive functionality has also been observed in some animal models.

Due to their anti-inflammatory properties, corticosteroids are used in the treatment of many diseases and conditions including asthma, systematic lupus erythematosus, rheumatoid arthritis, inflammatory bowel disease, nephritic syndrome, cancer, organ transplantation, autoimmune hepatitis, hypersensitivity reactions, cardiogenic and septic shock, glucocorticoid deficiency diseases (Addison's disease and panhypopituitarism), and multiple sclerosis. When the body experiences stress, the adrenal glands release corticosteroids, such as cortisol. Synthetic corticosteroids work by mimicking steroid hormones naturally produced by the adrenal glands. Upon release into the body's circulatory system, these hormones help to regulate inflammation as well as the body's immune response. Common synthetic corticosteroids include prednisone, cortisone, hydrocortisone, and methylprednisone. Supplementing the body's normal hormone levels with synthetic corticosteroids induces a genomic cascade that reduces inflammation and suppresses the immune response. This genomic cascade is initiated by the binding of steroids to intracellular glucocorticoid receptors (GRs) (Datson, N A et al. Identification of corticosteroid-responsive genes in rat hippocampus using serial analysis of gene expression. *European Journal of Neuroscience*. 2001; 14(4): 675-689).

Despite their widespread use and therapeutic benefit, synthetic corticosteroids often cause numerous adverse psychological, metabolic, and somatic side effects (Warrington T P, Bostwick J M. Psychiatric adverse effects of corticosteroids. *Mayo Clinic Proceedings*. 2006; 81(10)). Examples of such somatic side effects are displayed in Table 1. Psychological side effects include mood and anxiety disorders, behavioral disturbance, cognitive impairment, and psychosis.

TABLE 1

Somatic Side Effects of Corticosteroid Use

| | |
|---|---|
| Cardiovascular | Hypertension |
| | Accelerated atherosclerosis |
| Dermatologic | Acne |
| | Alopecia |
| | Hirsutism |
| | Striae |
| | Skin atrophy |
| | Purpura |
| Endocrine/Metabolic | Obesity |
| | Diabetes Mellitus |
| | Adrenal-pituitary axis suppression |
| | Hyperlipidemia |
| | Fluid and sodium retention |
| | Loss of potassium, calcium, and nitrogen |
| | Delayed growth |
| Neurologic | Pseudotumor cerebri |
| Gastrointestinal | Peptic ulcer disease |
| | Pancreatitis |
| | Fatty liver |
| Hematologic | Leukocytosis |
| | Neutrophilia |
| | Lymphophenia |
| Infectious | Oral candidiasis |
| | Increased risk of systemic infection |
| Musculoskeletal | Myopathy |
| | Osteoporosis |
| | Avascular necrosis |
| Ophthalmologic | Cataracts |
| | Glaucoma |

Cognitive impairment, anxiety and mood disorders are among the most common psychological side effects of corticosteroid use. Especially for patients who require long-term steroid treatment, these effects result in a diminished quality of life. For example, 33% of individuals taking corticosteroids (about 13 million) are reported to exhibit deficits in working or short-term memory, declarative memory, attention span and concentration (academic & occupational performance), and executive functioning (Stoudemire A, Anfinson T, Edwards J. Corticosteroid-induced delirium and dependency. *Gen Hosp Psychiatry.* 1984; 141: 369-372). In extreme cases, steroids can even induce delirium, dementia (persistent memory impairment), and mania (Varney N R, Alexander B, MacIndoe J H. Reversible steroid dementia in patients without steroid psychosis. *Am J Psychiatry.* 1984; 141:369-372).

Currently, there is no FDA approved drug designated for the treatment of the cognitive impairment and similar psychiatric disorders, such as anxiety and mood disorders, associated with corticosteroid use. Tricyclic antidepressants do not appear to be useful therapeutic agents to modulate the psychiatric side effects induced by steroids, and may actually exacerbate these symptoms (Lewis D A, Smith R E. Steroid-induced Psychiatric Syndromes: A Report of 14 Cases and a review of the Literature. *Journal of Affective Disorders.* 1983; 5: 319-332). In addition, there are no alternatives to corticosteroids for the treatment of inflammatory disorders—corticosteroids must be used.

The disclosure herein relates to more stable chemical formulations, crystalline salts and polymorphs thereof of tianeptine for use in the treatment of neurocognitive dysfunction and related psychiatric disorders induced by corticosteroid treatment. These disorders include trauma- and stressor-related disorders including PTSD and acute stress disorder; depressive disorders including major depressive disorder, persistent depressive disorder, bipolar depression, and premenstrual dysphoric disorder; neurodegenerative diseases such as Alzheimer's disease and multi-infarct dementia; and neurodevelopmental disorders including attention-deficit\hyperactivity disorder. The present disclosure can also be used in the treatment of asthma and chronic obstructive pulmonary disorder.

SUMMARY OF THE INVENTION

In some aspects, the disclosure herein comprises an oxalate salt/co-crystal (tianeptine oxalate) of (RS)-7-(3-chloro-6-methyl-6,11-dihydrodibenzo[c,f] [1,2]thiazepin-11-ylamino)heptanoic acid S,S-dioxide (tianeptine) as shown in Formula I, including crystalline and polymorph forms:

Formula I

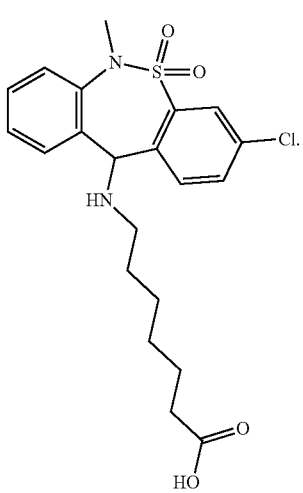

The tianeptine hemi-oxalate salt is shown as Formula (II):

Formula II

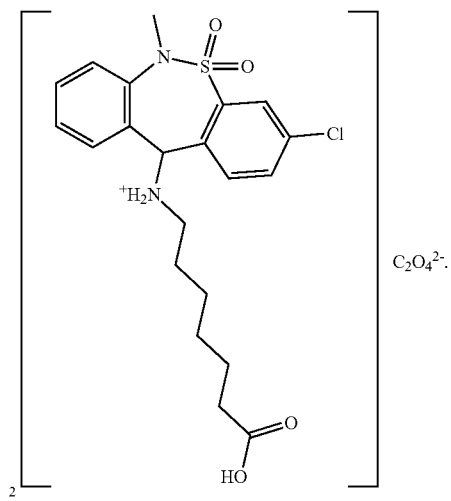

DETAILED DESCRIPTION OF THE EMBODIMENTS

The present disclosure relates to salt/co-crystal forms of tianeptine oxalate, more particularly tianeptine hemi-oxalate and/or tianeptine mono-oxalate. The properties of the salts/co-crystals of tianeptine are improved relative to one or more known forms of tianeptine, such as tianeptine free base or tianeptine sodium (the currently available form of tianeptine). The salts/co-crystals can take several forms including, but not limited to, hydrates and solvates as well as various stoichiometric ratios of tianeptine to oxalic acid. The disclosure also includes other forms of tianeptine oxalate including, but not limited to, polymorphs and amorphous forms. The disclosure also provides pharmaceutical compositions comprising the salts/co-crystals of tianeptine oxalate, methods of making those salts/co-crystals, and related methods of treatment.

One embodiment of this disclosure is an oxalate salt/co-crystal (tianeptine oxalate).

In some embodiments, the tianeptine oxalate is crystalline.

In some embodiments, the salt/co-crystal is crystalline tianeptine hemi-oxalate Form A, tianeptine mono-oxalate Form A, tianeptine mono-oxalate Form B, or mixtures thereof.

In some embodiments, the salt/co-crystal is anhydrous crystalline tianeptine hemi-oxalate Form A, tianeptine mono-oxalate Form A, tianeptine mono-oxalate Form B, or combinations thereof.

A pharmaceutical composition comprising the salt/co-crystal of tianeptine oxalate and a pharmaceutically acceptable carrier, diluent or excipient.

In some embodiments, the salt/co-crystal of the pharmaceutical composition is anhydrous crystalline tianeptine hemi-oxalate Form A, mono-oxalate Form A, or a combination thereof.

In some embodiments, the salt/co-crystal of the pharmaceutical composition is tianeptine hemi-oxalate Form A.

In some embodiments, the anhydrous crystalline tianeptine hemi-oxalate Form A exhibits an X-ray diffraction pattern (XRPD) comprising at least one peak at about 8.2, 8.6, 9.1, and 9.5 degrees 2θ.

In some embodiments, the anhydrous crystalline tianeptine hemi-oxalate Form A exhibits an XRPD pattern comprising at least one peak at about 8.2, 8.6, 9.1, and 9.5 degrees 2θ with an associated tolerance of 0.3 degrees 2θ.

In some embodiments, the anhydrous crystalline tianeptine hemi-oxalate Form A exhibits an XRPD pattern further comprising at least one peak selected from the group consisting of about 4.5, 8.2, 8.6, 9.1, 9.5, 11.5, 14.2, 15.2, 15.8, 16.4, 19.2, 22.1, 23.9, 26.9, and 27.4 degrees 2θ.

Figure 2:
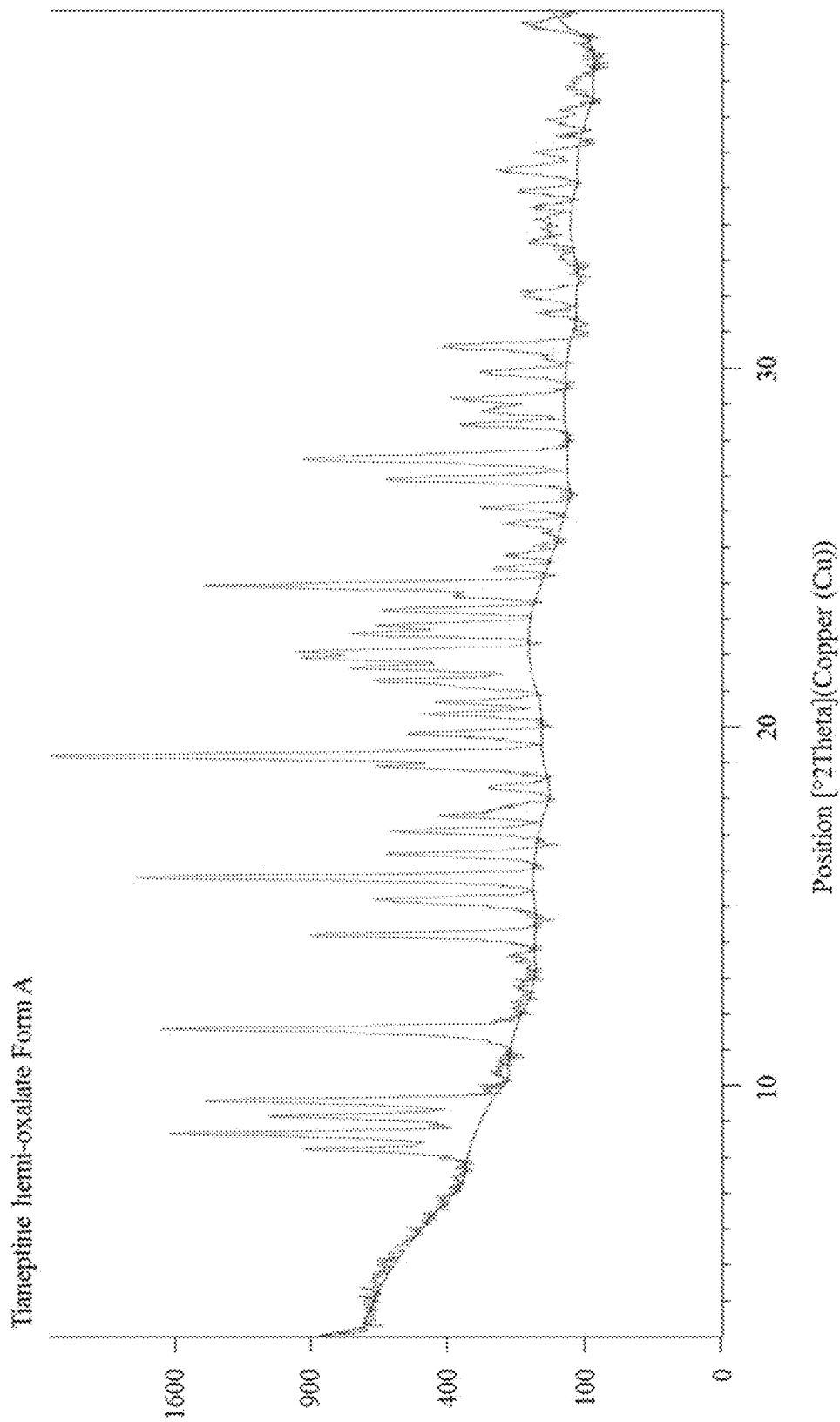
FIG. 2: XRPD pattern of tianeptine hemi-oxalate Form A.

In some embodiments, the anhydrous tianeptine hemi-oxalate crystalline Form A exhibits an XRPD pattern substantially the same as FIG. 2.

Figure 5:
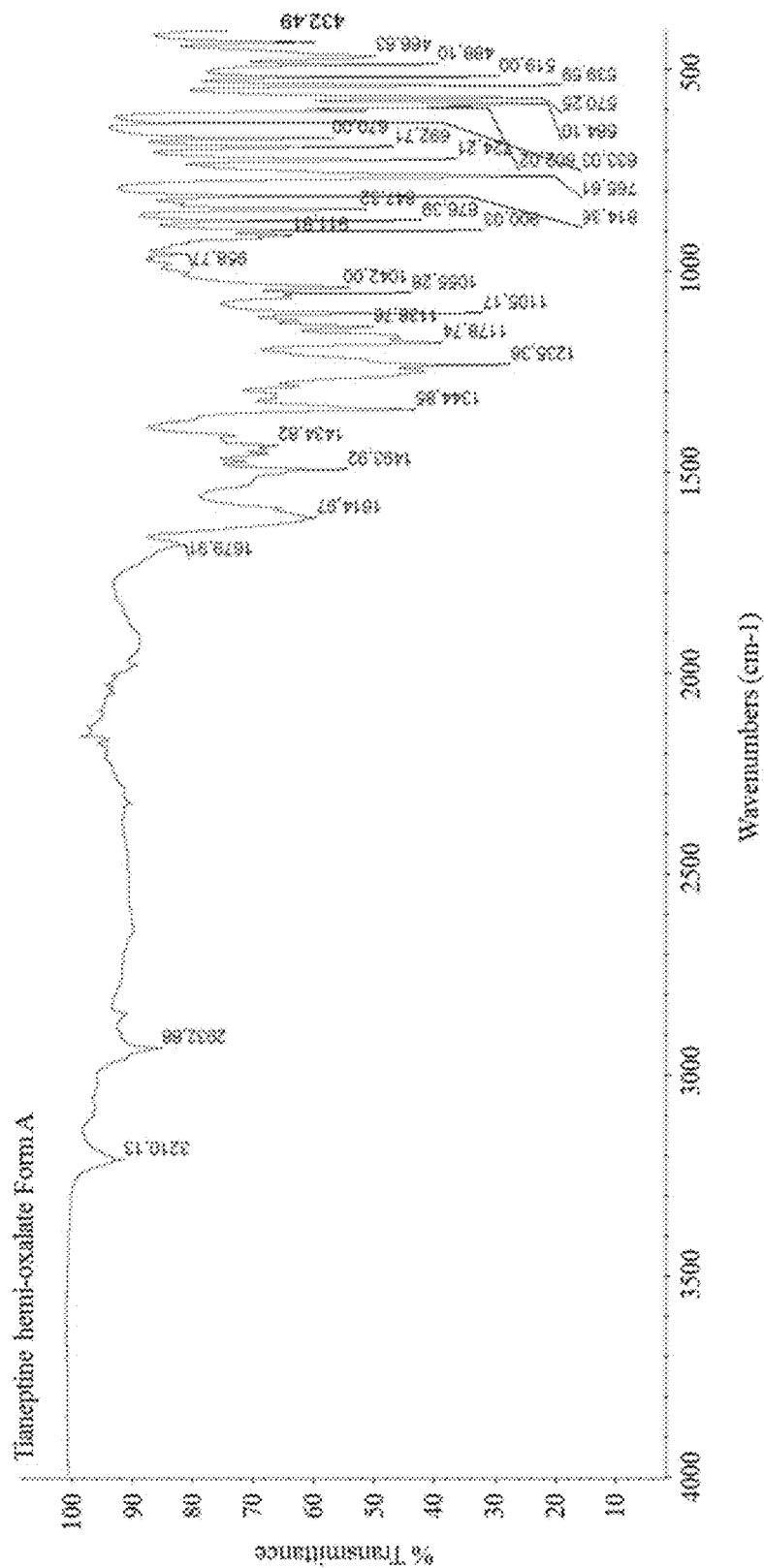
FIG. 5: FTIR spectrum of tianeptine hemi-oxalate Form A.
Figure 6:
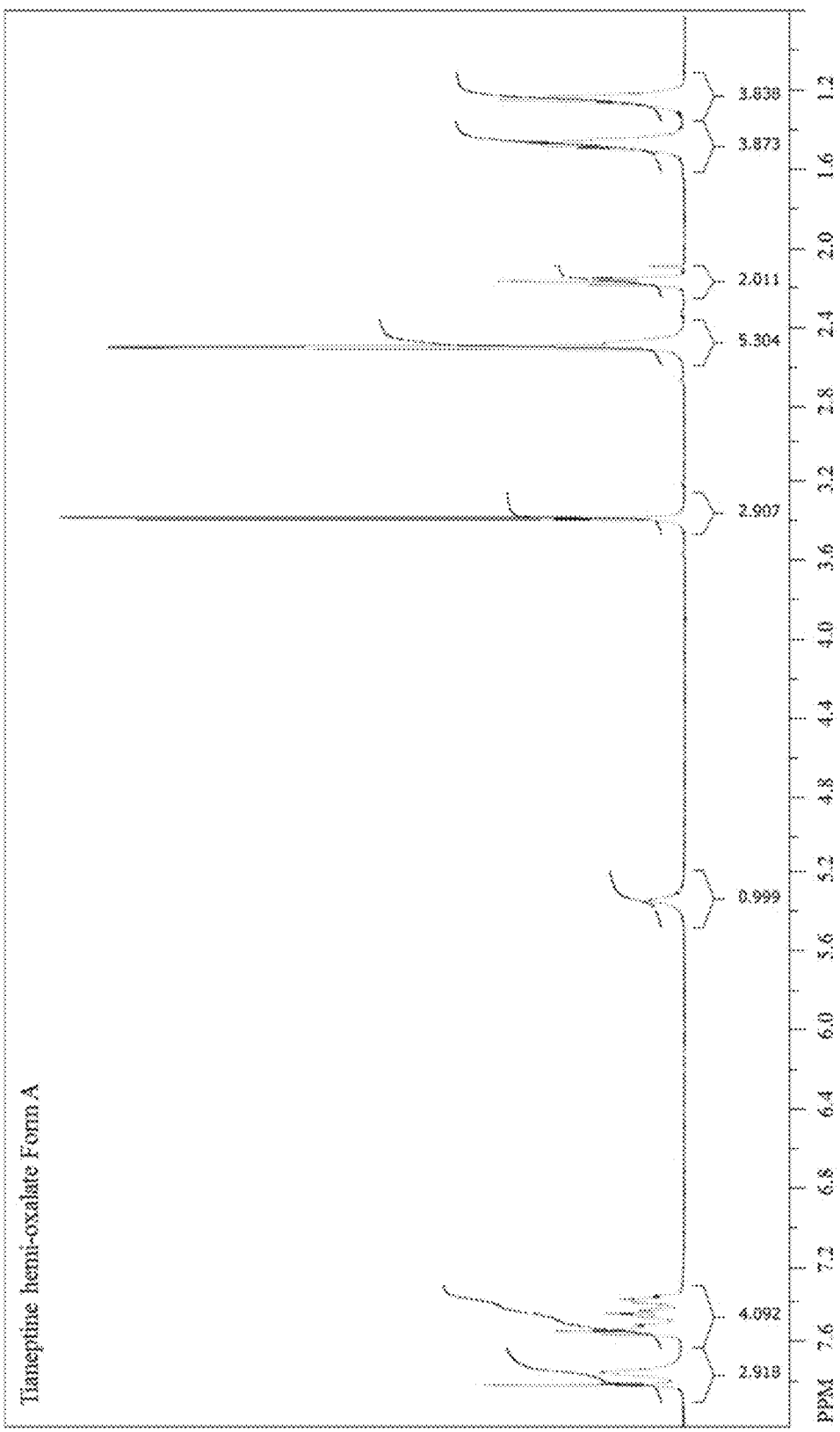
FIG. 6: 1H NMR spectrum (in DMSO-$d_6$) of tianeptine hemi-oxalate Form A.

In some embodiments, the anhydrous crystalline tianeptine hemi-oxalate Form A is characterized by at least one of a) an XRPD pattern exhibiting at least four of the peaks shown in FIG. 2; b) an FT-IR spectrum substantially the same as FIG. 5; and c) an NMR spectrum substantially the same as FIG. 6.

In some embodiments, the crystalline form is a tianeptine mono-oxalate Form A.

In some embodiments, the anhydrous crystalline tianeptine mono-oxalate Form A exhibits an X-ray diffraction pattern (XRPD) comprising at least one peak at about 10.2 and 10.5 degrees 2θ.

In some embodiments, the anhydrous crystalline tianeptine mono-oxalate Form A exhibits an X-ray diffraction pattern (XRPD) comprising at least one peak at about 10.2 and 10.5 degrees 2θ with an associated tolerance of 0.3 degrees 2θ.

In some embodiments, the anhydrous crystalline tianeptine mono-oxalate Form A exhibits an XRPD pattern further comprising at least one peak selected from the group consisting of about 7.5, 8.3, 10.2, 10.5, 11.9, 14.7, 16.2, 16.3, 17.9, 18.7, 21.0, 21.7, and 22.1 degrees 2θ.

Figure 10:
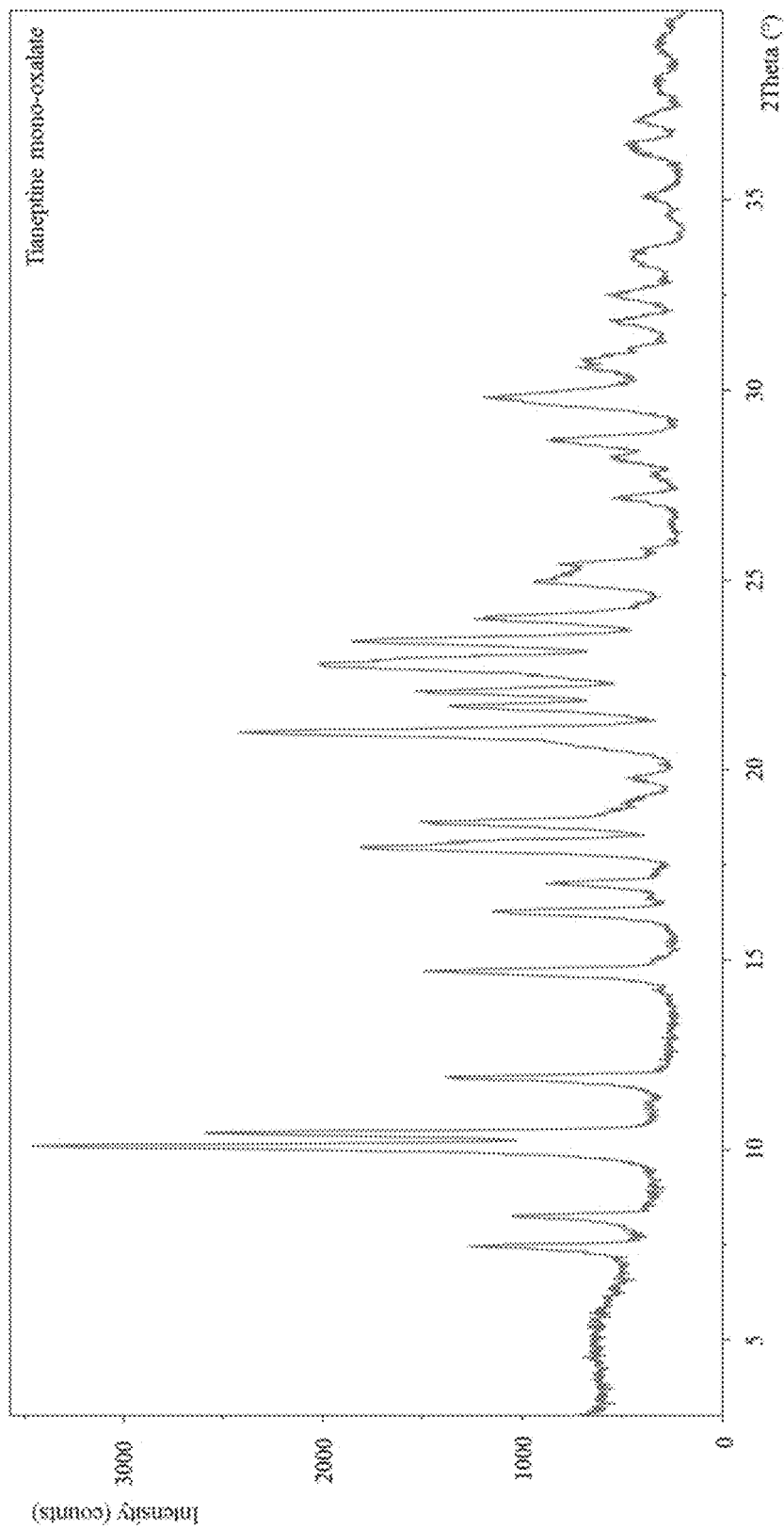
FIG. 10: XRPD pattern of tianeptine mono-oxalate Form A.

In some embodiments, the anhydrous crystalline tianeptine mono-oxalate Form A exhibits an XRPD pattern substantially the same as FIG. 10.

Figure 11:
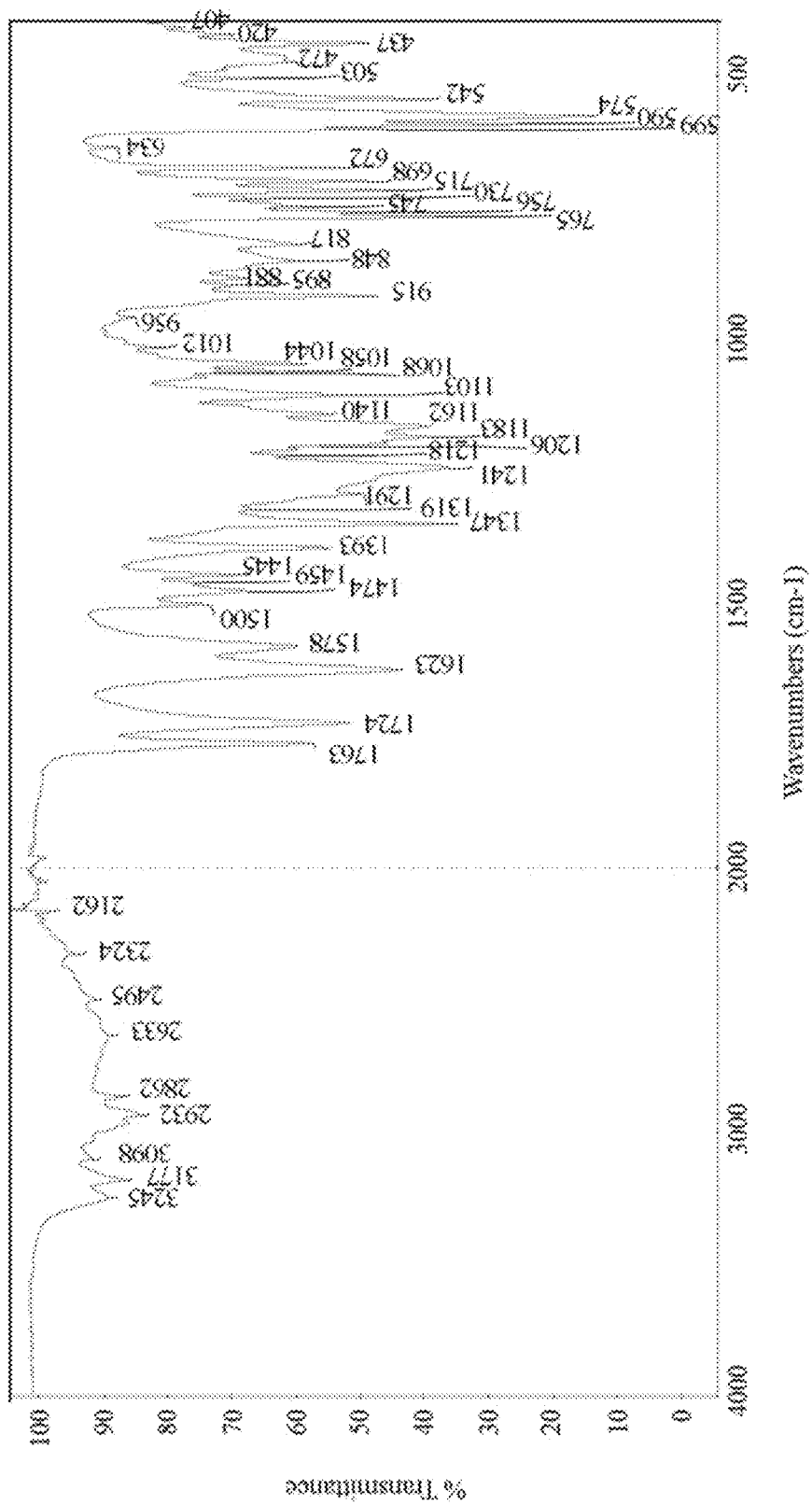
FIG. 11: FT-IR spectrum for tianeptine mono-oxalate Form A.

In some embodiments, the anhydrous crystalline tianeptine mono-oxalate Form A is characterized by at least one of a) an XRPD pattern exhibiting at least four of the peaks shown in FIG. 10; and b) an FT-IR spectrum substantially the same as FIG. 11.

In some embodiments, the crystalline form is a tianeptine mono-oxalate Form B.

In some embodiments, the anhydrous crystalline tianeptine mono-oxalate Form B exhibits an X-ray diffraction pattern (XRPD) comprising at least one peak at about 10.4 and 10.8 degrees 2θ.

In some embodiments, the anhydrous crystalline tianeptine mono-oxalate Form B exhibits an X-ray diffraction pattern (XRPD) comprising at least one peak at about 10.4 and 10.8 degrees 2θ with an associated tolerance of 0.3 degrees 2θ.

In some embodiments, the anhydrous crystalline tianeptine mono-oxalate Form B exhibits an XRPD pattern further comprising at least one peak selected from the group consisting of about 7.4, 7.8, 10.4, 10.8, 13.7, 14.8, 15.6, 16, 17.5, 19.9, 21.0, 20.2, 20.4, 20.9, 21.3, 21.6 and 21.9 degrees 2θ.

Figure 14:
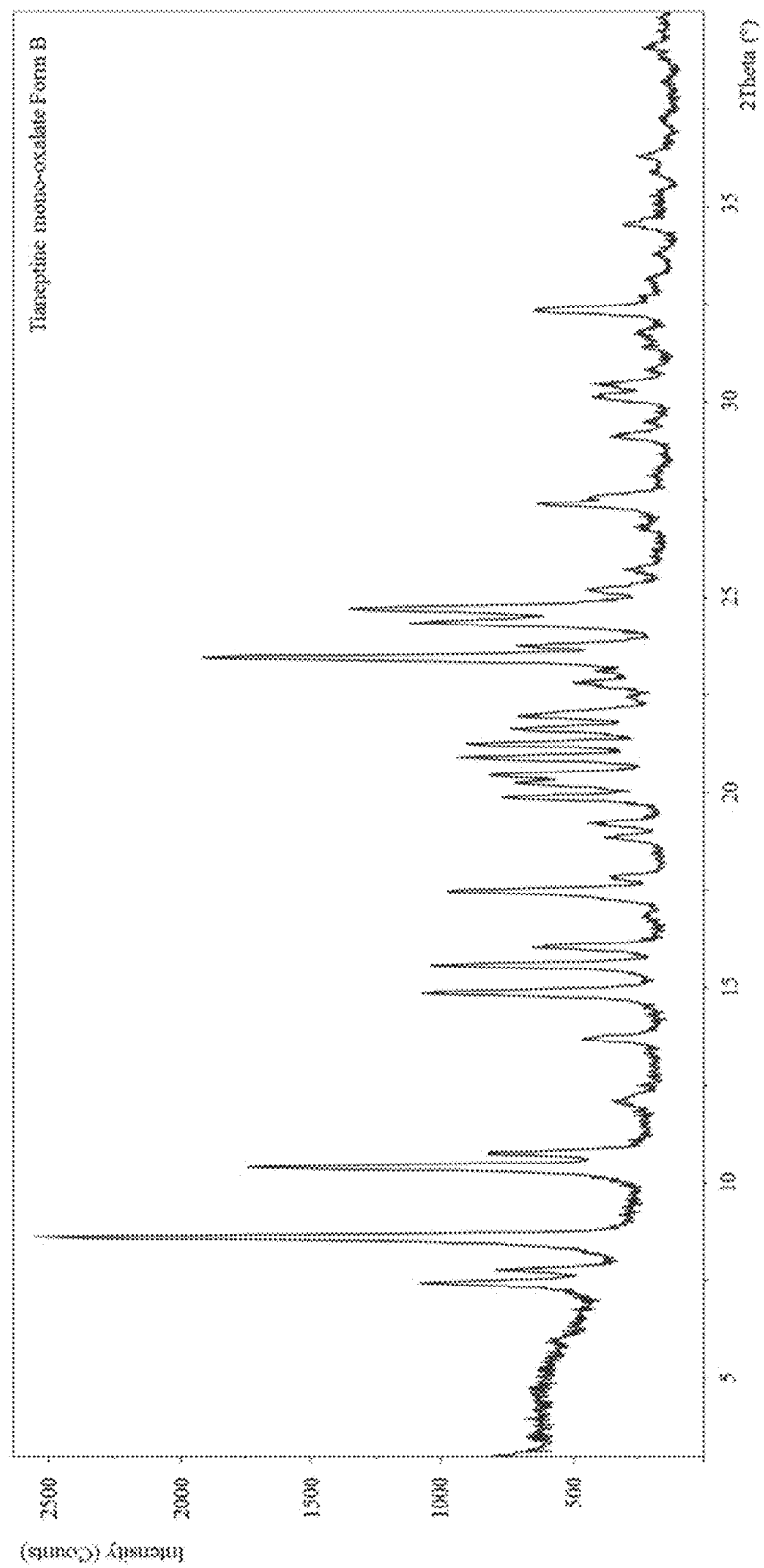
FIG. 14: XRPD pattern of tianeptine mono-oxalate Form B.

In some embodiments, the anhydrous crystalline tianeptine mono-oxalate Form B exhibits an XRPD pattern substantially the same as FIG. 14.

Figure 15:
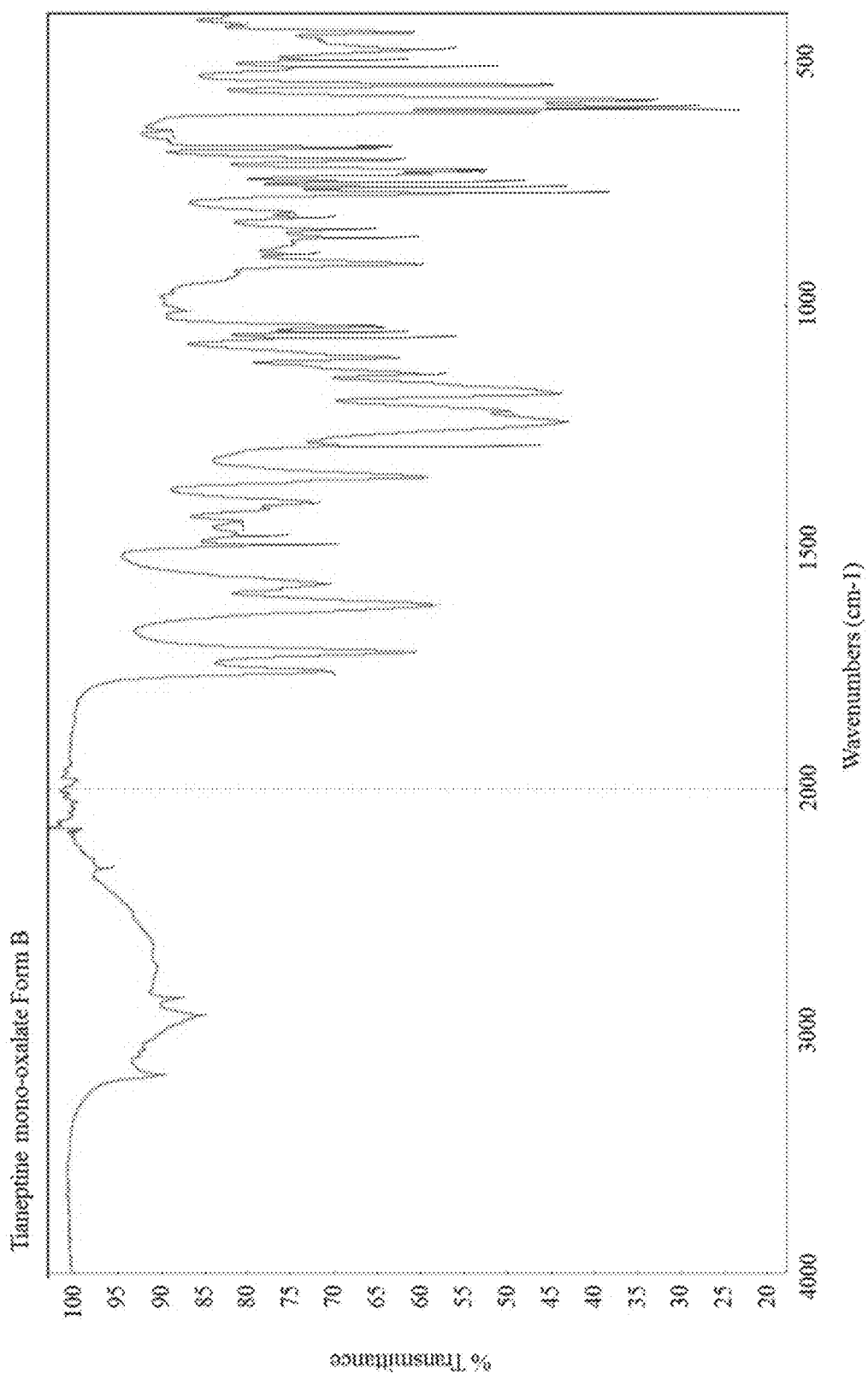
FIG. 15: FT-IR spectrum of tianeptine mono-oxalate Form B.

In some embodiments, the anhydrous crystalline tianeptine mono-oxalate Form B is characterized by at least one of a) an XRPD pattern exhibiting at least four of the peaks shown in FIG. 14; and b) an FT-IR spectrum substantially the same as FIG. 15.

In some embodiments, the pharmaceutical composition is in a solid form, a liquid form, a suspension form, a sustained release form, a delayed release form, or an extended release form.

In some embodiments, the anhydrous tianeptine oxalate crystalline form comprises a mixture of tianeptine hemi-oxalate Form A and tianeptine mono-oxalate Form A.

In some embodiments, the anhydrous tianeptine oxalate crystalline form comprises a mixture of tianeptine hemi-oxalate Form A and tianeptine mono-oxalate Form A, wherein the anhydrous tianeptine oxalate crystalline form exhibits an XRPD pattern comprising at least one peak selected from the group consisting of about 10.2 and 10.5 degrees 2θ.

In some embodiments, the anhydrous tianeptine oxalate crystalline form comprises a mixture of tianeptine hemi-oxalate Form A and tianeptine mono-oxalate Form A, wherein the anhydrous tianeptine oxalate crystalline form exhibits an XRPD pattern comprising at least one peak selected from the group consisting of about 10.2 and 10.5 degrees 2θ with an associated tolerance of 0.3 degrees 2θ.

In some embodiments, the anhydrous tianeptine oxalate crystalline form comprises a mixture of tianeptine hemi-oxalate Form A and tianeptine mono-oxalate Form A, wherein the crystalline form exhibits an XRPD pattern further comprising at least one peak selected from the group consisting of about 7.5, 8.3, 10.2, 10.5, 11.9, 14.7, 16.2, 16.3, 17.9, 18.7, 21.0, 21.7, and 22.1 degrees 2θ.

Figure 9:
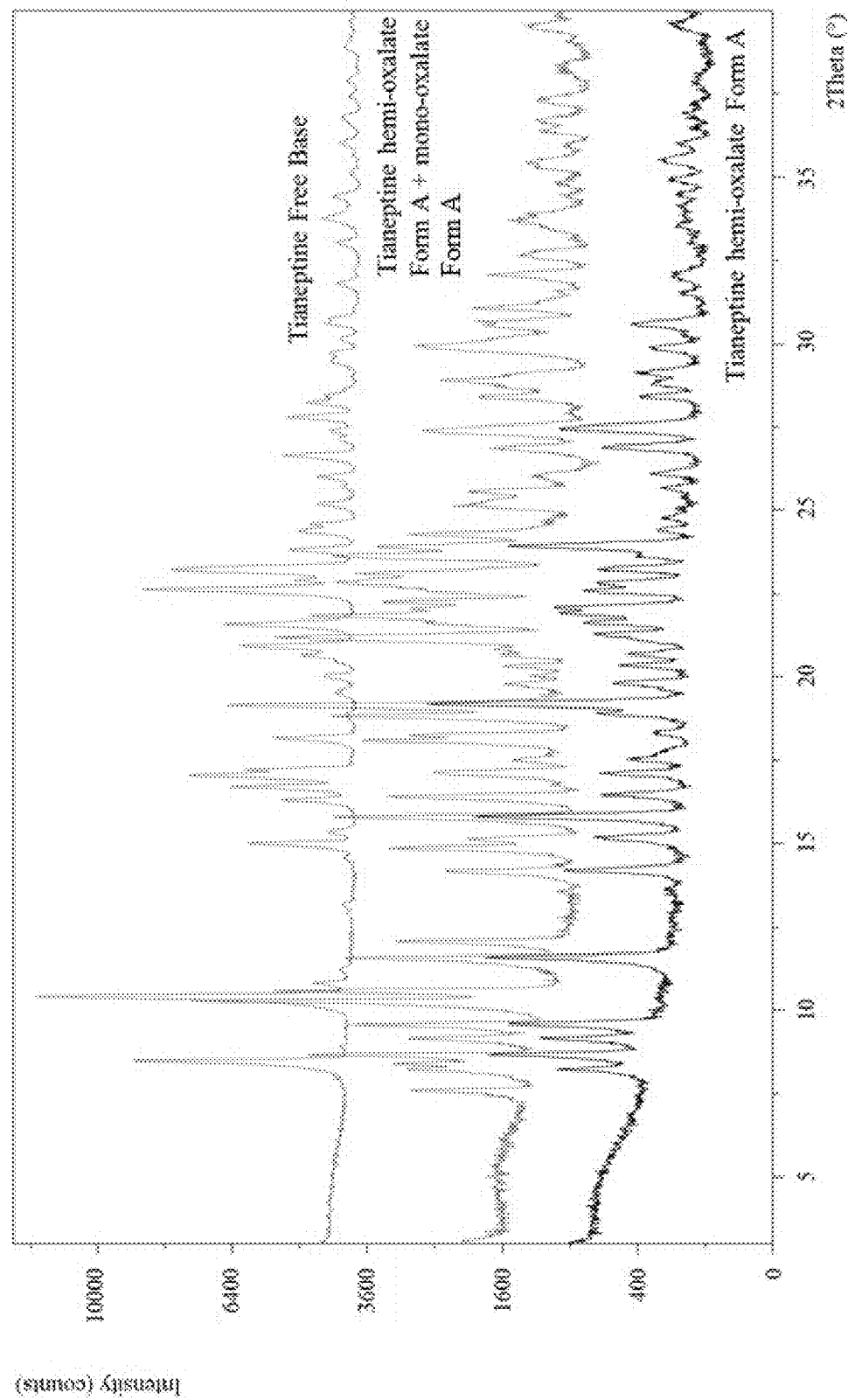
FIG. 9: XRPD comparison between tianeptine free base, tianeptine hemi-oxalate Form A, and tianeptine hemi-oxalate Form A+tianeptine mono-oxalate Form A.

In some embodiments, the anhydrous tianeptine oxalate crystalline form comprises a mixture of tianeptine hemi-oxalate Form A and tianeptine mono-oxalate Form A, wherein the crystalline form exhibits an XRPD pattern substantially the same as FIG. 9.

The salt/co-crystal forms of the various embodiments of this disclosure provide improved stability, bioavailability, lower hygroscopicity, more consistent pK, and easier processing and manufacturing, including pharmaceutical compositions as compared to sodium tianeptine.

In one aspect, this disclosure also provides formulations of tianeptine oxalate salts to be developed as first generation therapy for the treatment of corticosteroid-induced psychological side effects.

The tianeptine oxalate in the salt/co-crystal forms of the various embodiments of the disclosure has a higher melting point than the formulation of tianeptine (Stablon®) currently used to treat depression, suggesting greater crystalline stability and thus improved product performance in tablet form. As such, tianeptine oxalate has easier tablet formation as compared to Stablon® and improved tolerability such as fewer adverse events and severe adverse events.

In some embodiments of this disclosure, the tianeptine hemi-oxalate (Form A) and/or mono-oxalate (Form A and/or Form B) salts can be incorporated into a pharmaceutical composition. In some embodiments, the composition is in any one the following forms: sustained release, controlled release, delayed release or extended release. In some embodiments, the tianeptine hemi-oxalate and/or mono-oxalate mixtures can be incorporated into a hydrophilic matrix system with a polymer. The tianeptine hemi-oxalate and/or mono-oxalate mixtures are released by dissolution, diffusion and/or erosion from the hydrophilic matrix when the polymer swells on contact with the aqueous medium to form a gel layer on the surface of the system.

In another embodiment, the tianeptine hemi-oxalate (Form A) and/or mono-oxalate (Form A and/or Form B) can be incorporated into a pharmaceutical composition comprising two or more layers of tianeptine hemi-oxalate and/or oxalate such that one layer is substantially released prior to the substantial release of another layer in vivo. In another embodiment, the hemi-oxalate and/or oxalate salt of tianeptine can be incorporated into a pharmaceutical composition comprising pellets, wherein the pellets have varying extents or compositions of coating so as to enable release of tianeptine over a substantially longer period of time than that of the currently available tianeptine (e.g., STABLON, Coaxil, or Tatinol).

In another embodiment, the hemi-oxalate (Form A) and/or mono-oxalate (Form A and/or Form B) salt of tianeptine can be incorporated into an osmotically active pharmaceutical composition suitable for oral administration. Osmotically active pharmaceutical compositions, osmotic pumps, osmotic drug delivery, and other osmotic technology suitable for oral administration can include, but are not limited to, OROS® Push-Pull and OROS® Tri-layer pharmaceutical compositions. In another embodiment, the tianeptine hemi-oxalate (Form A) and/or mono-oxalate (Form A and/or Form B) salt of tianeptine can be incorporated into an OROS® drug delivery system. Such controlled release pharmaceutical compositions comprising the oxalate salt of tianeptine, such as an osmotically active pharmaceutical composition suitable for oral administration, may lead to a longer lasting therapeutic effect than that of tianeptine sodium salt in the currently marketed form.

In some embodiments, the compositions of this disclosure may be in solid dosage forms such as capsules, tablets, dragrees, pills, lozenges, powders and granule. Where appropriate, they may be prepared with coatings such as enteric coatings or they may be formulated so as to provide controlled releases of one or more active ingredient such as sustained or prolonged release according to methods well known in the art. In certain embodiments, the composition is in form of a slow, controlled, or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release", "prolonged release", "sustained release", or "slow release", as these terms are used in the pharmaceutical sciences. The composition may also be in liquid dosage forms including solutions, emulsions, suspensions, syrups, and elixirs. The composition may be formulated for once daily administration.

INSTRUMENTAL TECHNIQUES

Instrumental Techniques

Identification of the crystalline forms obtained by the present invention can be made by methods known in the art, including but not limited to X-Ray powder diffraction (XRPD), Fourier Transform Infrared (FT-IR) spectra, Differential Scanning calorimetry (DSC), Thermogravimetric Analysis (TGA), and Nuclear Magnetic Resonance (NMR). Furthermore, it should be understood that operator, instrument and other related changes may result in some margin of error with respect to analytical characterization of the salts/co-crystals.

Differential Scanning Calorimetry:

The analysis was carried out on the untreated sample using a DSC Mettler Toledo DSC1. The sample was weighed in an aluminum pan hermetically sealed with an aluminum cover. The analysis was performed by heating the sample from 25° C. to 350° C. at 10 K/min.

TABLE 2

| Technical Specification | |
| --- | --- |
| Temperature range | −170° C. 600° C. |
| Heating rates | 0.001 K/min 100 K/min |
| Cooling rate | 0.001 K/min 100 K/min (depending on temperature) |
| Sensor | Heat flux system |
| Measurement range | 0 mW ± 600 mW |
| Temperature accuracy | 0.1 K |
| Enthalpy accuracy | Generally <1% |
| Cooling options | Forced air (down to RT), LN2 (down to −170° C.) |
| Purge gas rate | 60 mL/min |
| Intracooler for the extended rate | −40° C. 600° C. |

Thermogravimetric Analysis:

The TG analysis was carried out on an untreated sample using the Mettler Toledo TGA/DSC1. The sample was weighed in an aluminum pan hermetically sealed with an aluminum pierced cover. The analysis was performed by heating the sample from 25° C. to 450° C. at 10 K/min.

TABLE 3

| Temperature Data | |
|---|---|
| Temperature range | RT 1100° C. |
| Temperature accuracy | 1 K |
| Temperature precision | ±0.4 K |
| Heating rate | 0.02 250 K/min |
| Cooling time | 20 min (1100° C. 100° C.) |
| Sample volume | ≤100 μL |

TABLE 4

| Special modes | |
|---|---|
| Automation | 34 sample positions |
| TGA-FTIR | Coupled with Thermo Nicolet iS10 spectrometer |
| Balance data | XP5 |
| Measurement range | ≤5 g |
| Resolution | 1.0 μg |
| Weighing accuracy | 0.005% |
| Weighing precision | 0.0025% |
| Internal ring weights | 2 |
| Blank curve reproducibility | Better than ±10 μg over the whole temperature range |

X-Ray Powder Diffraction (XRPD):

X-ray powder diffraction patterns were obtained using an X'Pert PRO PANalytical X-ray Diffractometer.

The X'Pert PRO PANalytical X-ray Diffractometer was equipped with a copper source ($Cu/K_\alpha$ 1.5406 Å). Diffractogram was acquired using control software (X'Pert Data Collector vs. 2.2d) under ambient conditions at a power setting of 40 kV at 40 mA in reflection mode, while spinning over 360 degrees at 1 degree/second.

TABLE 5

| (X-Ray Powder Diffraction (XRPD): Measurement Details) | |
|---|---|
| Measurement type: | Single scan |
| Sample mode: | Reflection |
| Scan | |
| Scan axis: | Gonio |
| Scan range (°): | 3.0010-39.9997 |
| Step size (°): | 0.0167 |
| Counting time (s): | 12.700 |
| No. of points: | 2214 |
| Scan mode: | Continuous |
| Used wavelength | |
| Intended wavelength type: | Kα1 |
| Kα1 (A): | 1.540598 |
| Kα2 (A): | 1.544426 |
| Kα2/Kα1 intensity ratio: | 0.50 |
| Kα (A): | 1.541874 |
| Kβ (A): | 1.392250 |
| Incident beam path | |
| Radius (mm): | 240.0 |

TABLE 6

| (X-Ray Powder Diffraction (XRPD): X-Ray Tube) | |
|---|---|
| Name: | PW3373/00 Cu LFF DK184511 |
| Anode material: | Cu |
| Voltage (kV): | 40 |
| Current (mA): | 40 |
| Focus | |
| Focus type: | Line |
| Length (mm): | 12.0 |
| width (mm): | 0.4 |
| Take-off angle (°): | 6.0 |
| Soller slit | |
| Name: | Soller 0.04 rad. |
| Opening (rad.): | 0.04 |
| Mask | |
| Name: | Inc. Mask Fixed 15 mm (MPD/MRD) |
| Width (mm): | 11.60 |
| Anti-scatter slit | |
| Name: | Slit Fixed ½° |
| Type: | Fixed |
| Height (mm): | 0.76 |
| Divergence slit | |
| Name: | Slit Fixed ¼° |
| Type: | Fixed |
| Height (mm): | 0.76 |
| Sample movement | |
| Movement type: | Spinning |
| Rotation time (s): | 1.0 |
| Diffracted beam path | |
| Radius (mm): | 240.0 |
| Anti-scatter slit | |
| Name: | Anti-Scatter Slit 5.0 mm |
| Type: | Fixed |
| Height (mm): | 5.00 |
| Soller slit | |
| Name: | Soller 0.04 rad. |
| Opening (rad.): | 0.04 |
| Filter | |
| Name: | Nickel |
| Thickness (mm): | 0.020 |
| Material: | Ni |

TABLE 7

| (X-Ray Powder Diffraction (XRPD): Detector) | |
|---|---|
| Name: | X'Celerator |
| Type: | RTMS detector |
| PHD - Lower level (%): | 39.5 |
| PHD - Upper level (%): | 80.0 |
| Mode: | Scanning |
| Active length (°): | 2.122 |

Fourier Transform Infrared Spectroscopy (FT-IR):

The analysis was carried out on an untreated sample using a Thermo Nicolet iS50-ATR module Spectrometer equipped with a Smart Performer Diamond, DTGS KBr Detector, IR Source, and KBr Beam splitter. The sample was measured using the parameters described the Table 8 below.

TABLE 8

| Experimental Conditions | |
|---|---|
| Resolution | 4000-650 cm−1 |
| Number of sample scans | 32 |
| Number of background scans | 32 |

TABLE 8-continued

Experimental Conditions

| | |
|---|---|
| Sample gain | 8 |
| Optical Velocity | 0.6329 |
| Aperture | 100.00 |

Nuclear Magnetic Resonance (NMR):

The 1H NMR spectra were acquired at ambient temperature on a Gemini Varian 400 MHz spectrometer. Samples were prepared for NMR spectroscopy as ~5-50 mg solutions in DMSO-d6. For each sample 16 transients with a delay of t1=1 sec were collected at 25° C.

Crystal Structure Data:

All crystal data were collected on an Oxford Xcalibur S instrument using Mo Kα radiation (λ=0.71073 Å) and a graphite monochromator at room temperature. SHELX97 was used for structure solution and refinement and was based on F2. Non-hydrogen atoms were refined anisotropically. Hydrogen atoms bound to carbon and nitrogen atoms were added in calculated positions. Hydroxyl hydrogen atoms were located using a Fourier map and their position refined. The program mercury was used for figure and calculation of X-ray powder patterns on the basis of single-crystal data.

Definitions

For the purposes of this specification and appended claims, unless otherwise indicated, all numbers expressing quantities, percentages or proportions, and other numerical values used in the specification and claims, are to be understood as being modified in all instances by the term "about." As used herein, the meaning of the term "about" depends upon the context in which it is used. When used with respect to the position of a peak on an X-ray powder diffraction (XRPD) pattern, the term "about" includes peaks within an associated tolerance of ±0.3 degrees 2θ. For example, as used herein, an XRPD peak at "about 10.0 degrees 2θ" means that the stated peak occurs from 9.7 to 10.3 degrees 2θ. When used with respect to the position of a peak on a solid state 13C NMR spectrum, the term "about" includes peaks within ±0.2 ppm of the stated position. For example, as used herein, a 13C NMR spectrum peak at "about 100.0 ppm" means that the stated peak occurs from 99.8 to 100.2 ppm. Accordingly, unless indicated to the contrary, the numerical parameters set forth in the following specification and attached claims are approximations that can vary depending upon the desired properties sought to be obtained.

As used herein, the term "substantially" in reference to an XRPD pattern refers to a spectrum having at least 4, 5, 6, 7, 8, 9, 10, 11, 12, 13, 14, or 15 peaks (perhaps differing in amplitude) in common with the referenced pattern; or a pattern having a tolerance of ±0.3 degrees 2θ within the referenced peaks. In reference to an NMR pattern, "substantially" refers to a spectrum having at least 4, 5, 6, 7, 8, 9, 10, 11, 12, 13, 14, or 15 peaks (perhaps differing in amplitude) in common with the referenced pattern; or a pattern having a tolerance of ±0.2 ppm within the referenced peaks. In reference to an FT-IR pattern, "substantially" refers to a spectrum having at least 4, 5, 6, 7, 8, 9, 10, 11, 12, 13, 14, or 15 peaks (perhaps differing in amplitude) in common with the referenced pattern; or a pattern having a tolerance of ±0.5 cm$^{-1}$ within the referenced peaks.

As used herein, the term "co-crystal" refers to a molecular adduct of two molecules, each of which is solid at room temperature. A tianeptine oxalate co-crystal is a molecular adduct of tianeptine and any one of oxalate, hemi-oxalate, and mono-oxalate. The two molecules of the adduct form hydrogen bonds without transferring hydrogen between the molecules.

As used in this specification and the appended claims, the singular forms "a," "an," and "the," include plural references unless expressly and unequivocally limited to one referent.

As used herein, the term "include" and its grammatical variants are intended to be non-limiting, such that recitation of items in a list is not to the exclusion of other like items that can be substituted or added to the listed items.

As used herein, the term "comprising" means including elements or steps that are identified following that term, but any such elements or steps are not exhaustive, and an embodiment can include other elements or steps.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

Example 1

Tianeptine Hemi-Oxalate Form A 100-1000 mg of (RS)-7-(3-chloro-6-methyl-6,11-dihydrodibenzo[c,f] [1,2]thiazepin-11-ylamino)heptanoic acid S,S-dioxide—the starting material (SM) and 20-200 mg of oxalic acid (1 eq.) were mixed in acetone (2-20 mL) and the solution was heated at 40-60° C. until total dissolution occurred. The clear solution was cooled at room temperature and stirred for 12-24 hours. The white precipitate was recovered under vacuum, washed with acetone and dried at 40-60° C. for 12-24 hours.

TABLE 9

Characterization details of Tianeptine Hemi-Oxalate Form A

| Techniques/ experiment | Results for Tianeptine Hemi Oxalate Form A |
|---|---|
| Synthesis | Tianeptine hemi oxalate Form A was prepared by precipitation from an acetone solution of tianeptine and oxalic acid |
| XRPD | The evidenced crystalline form was labeled as Form A |
| FT-IR | The infrared spectrum confirmed the formation of a new species |
| DSC | The DSC profile showed an endothermic peak at approximately 205° C. (Onset 204.43° C.). |
| TGA | The TGA profile was typical of an anhydrous compound decomposing above 200° C. EGA showed the evolution of $CO_2$ confirming the presence of the coformer |

TABLE 9-continued

Characterization details of Tianeptine Hemi-Oxalate Form A

| Techniques/experiment | Results for Tianeptine Hemi Oxalate Form A |
|---|---|
| 1H-NMR | 1H-NMR confirmed the structural integrity of the tianeptine whereas the coformer was not visible. The protons of the molecule underwent slight shifts in their resonance frequencies |

DSC/TGA

Figure 3:
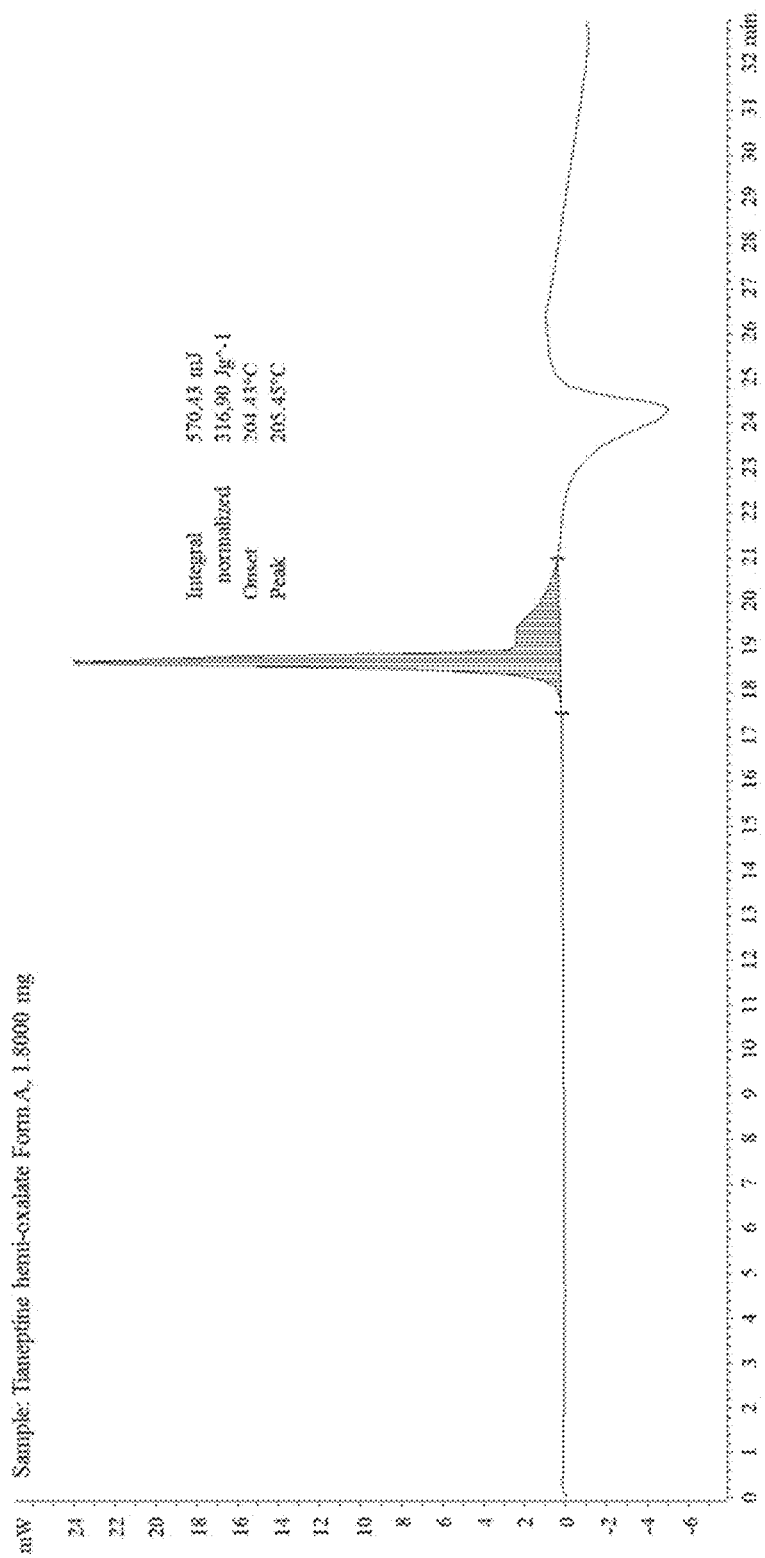
FIG. 3: DSC profile of tianeptine hemi-oxalate Form A.

The DSC profile of tianeptine hemi-oxalate Form A as illustrated in FIG. 3 was characterized by an endothermic event which took place just before sample decomposition. The peak at 205° C. (Onset 204.43° C.) was due to the sample melting and the broad shoulder was associated with decomposition.

Figure 4:
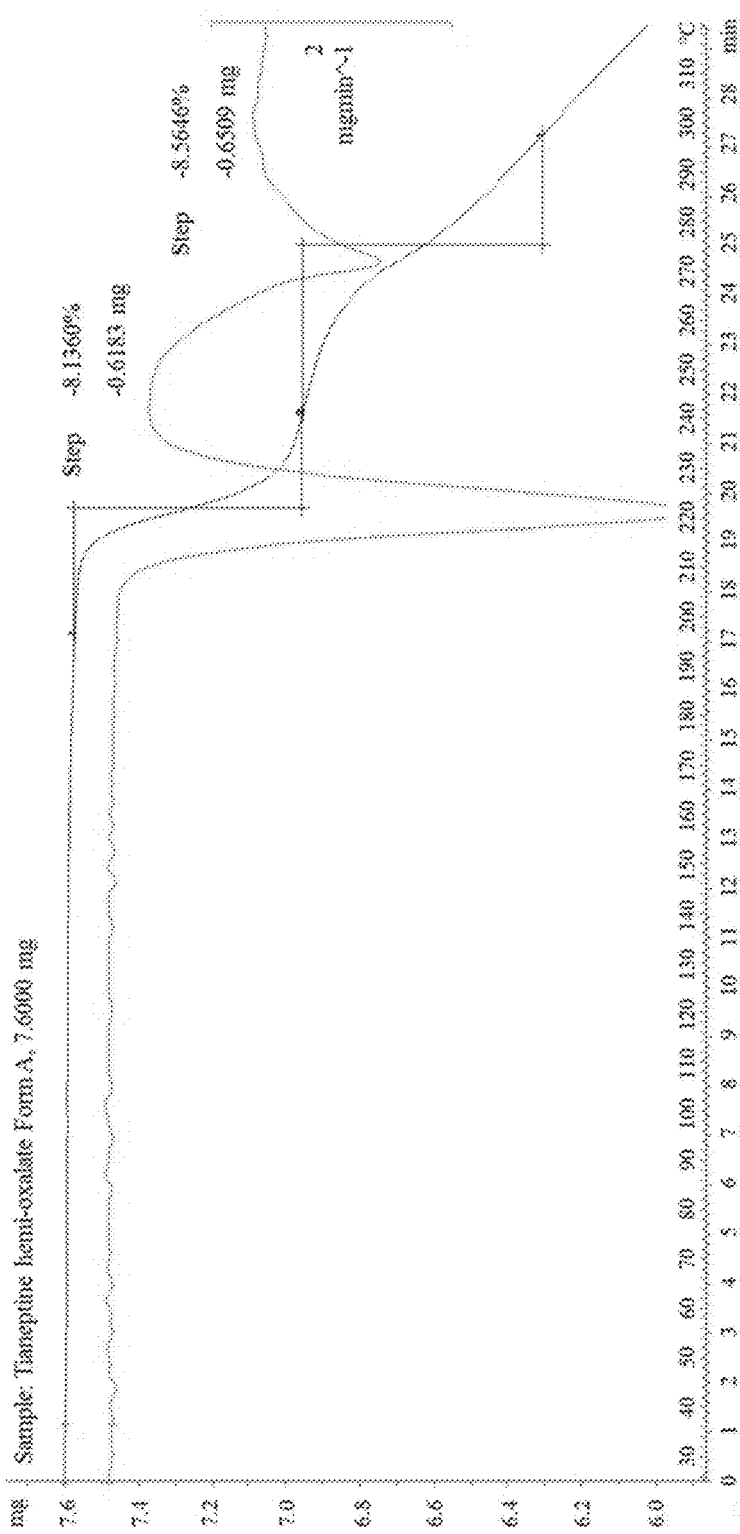
FIG. 4: TGA profile of tianeptine hemi-oxalate Form A.

The TGA profile of tianeptine hemi-oxalate Form A as illustrated in FIG. 4 is typical of an anhydrous compound. Sample decomposition was characterized by the first weight loss of 8.13% w/w, which corresponded to 0.5 equivalents of oxalic acid. A stoichiometry of 1:0.5 between tianeptine:oxalic acid was suggested. The oxalate showed a very high melting point above the 200° C., when the melting and decomposition occurred at the same time.

XRPD

Figure 1:
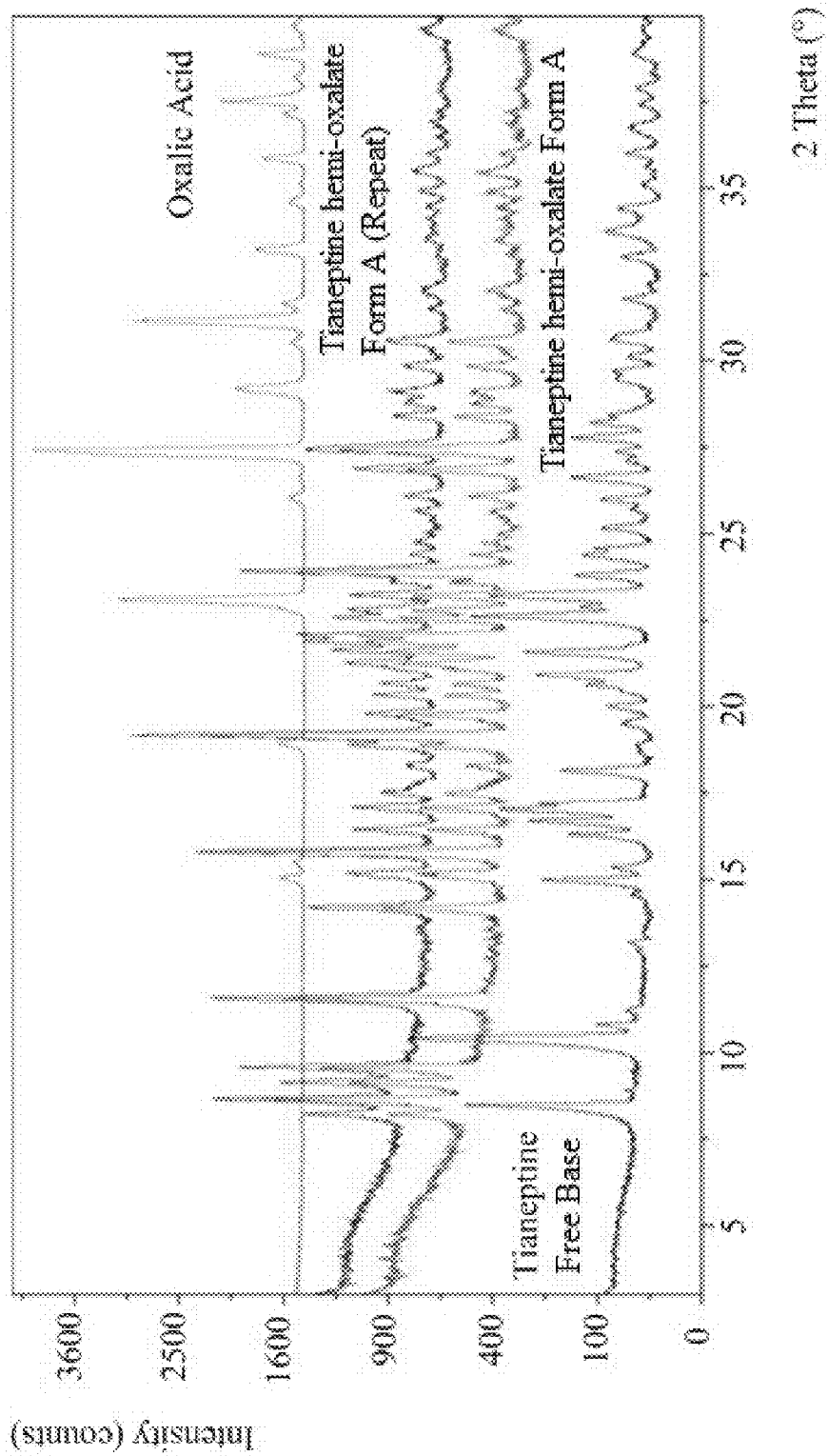
FIG. 1: Overlayed XRPD patterns of tianeptine hemi-oxalate Form A, tianeptine free base and oxalic acid.

FIGS. 1 and 2 illustrate the XRPD pattern of the tianeptine hemi-oxalate salt.

TABLE 10

XRPD peaks list of Tianeptine hemi-oxalate Form A

| Pos. [°2Th.] | Height [cts] | FWHM [°2Th.] | d-spacing [Å] | Rel. Int. [%] |
|---|---|---|---|---|
| 4.5010 | 34.97 | 0.9368 | 19.63245 | 1.56 |
| 8.2252 | 607.21 | 0.0669 | 10.74980 | 27.02 |
| 8.6666 | 1323.95 | 0.1004 | 10.20325 | 58.92 |
| 9.1460 | 799.69 | 0.0836 | 9.66947 | 35.59 |
| 9.5853 | 1166.90 | 0.1004 | 9.22727 | 51.93 |
| 11.5807 | 1467.88 | 0.1004 | 7.64149 | 65.33 |
| 14.1914 | 714.49 | 0.1004 | 6.24106 | 31.80 |
| 15.2018 | 454.39 | 0.0836 | 5.82843 | 20.22 |
| 15.7987 | 1647.80 | 0.1338 | 5.60952 | 73.33 |
| 16.4473 | 422.17 | 0.1004 | 5.38976 | 18.79 |
| 19.1657 | 2246.97 | 0.1506 | 4.63098 | 100.00 |
| 22.0891 | 773.13 | 0.0836 | 4.02427 | 34.41 |
| 23.9294 | 1253.33 | 0.1840 | 3.71878 | 55.78 |
| 26.8794 | 476.25 | 0.1673 | 3.31697 | 21.20 |
| 27.4168 | 751.73 | 0.1338 | 3.25317 | 33.46 |
| 28.3866 | 229.43 | 0.1171 | 3.14419 | 10.21 |
| 28.7606 | 152.29 | 0.1673 | 3.10416 | 6.78 |
| 29.1253 | 224.40 | 0.1171 | 3.06611 | 9.99 |
| 29.8763 | 174.82 | 0.1673 | 2.99072 | 7.78 |
| 30.6136 | 287.62 | 0.1171 | 2.92035 | 12.80 |
| 31.5515 | 44.50 | 0.1171 | 2.83565 | 1.98 |
| 32.1254 | 89.62 | 0.2676 | 2.78629 | 3.99 |
| 33.5303 | 64.44 | 0.1673 | 2.67270 | 2.87 |
| 34.4758 | 64.22 | 0.1338 | 2.60153 | 2.86 |
| 34.9300 | 96.39 | 0.1673 | 2.56873 | 4.29 |
| 35.4906 | 138.82 | 0.2007 | 2.52944 | 6.18 |
| 36.0079 | 82.53 | 0.1004 | 2.49428 | 3.67 |
| 36.4741 | 23.82 | 0.1004 | 2.46346 | 1.06 |
| 36.9223 | 65.21 | 0.1004 | 2.43458 | 2.90 |
| 37.8937 | 29.49 | 0.4684 | 2.37437 | 1.31 |
| 39.6005 | 74.60 | 0.2676 | 2.27588 | 3.32 |

The FT-IR spectrum and peaks of tianeptine hemi-oxalate Form A are illustrated in FIG. 5 and Table 11. Comparison with the starting material showed many differences including the disappearance of the NH stretching at 3300 cm$^{-1}$ and the appearance of the broad band at 1615 cm$^{-1}$ from the C=O stretching ascribable to the presence of the oxalate.

TABLE 11

FT-IR Peak List of Tianeptine hemi-Oxalate Form A

| Position (cm−1) | Intensity [% T] |
|---|---|
| 432.49 | 62.178 |
| 466.63 | 50.071 |
| 488.10 | 54.917 |
| 519.00 | 60.449 |
| 539.59 | 38.578 |
| 570.25 | 27.820 |
| 584.10 | 25.441 |
| 602.02 | 50.697 |
| 633.03 | 83.567 |
| 670.00 | 56.310 |
| 692.71 | 61.686 |
| 724.21 | 47.215 |
| 765.61 | 28.950 |
| 814.36 | 71.754 |
| 847.32 | 51.291 |
| 876.39 | 70.707 |
| 900.03 | 63.088 |
| 911.81 | 64.771 |
| 958.77 | 81.157 |
| 1042.00 | 54.177 |
| 1055.28 | 61.901 |
| 1105.17 | 50.022 |
| 1138.76 | 50.102 |
| 1178.74 | 39.915 |
| 1235.36 | 39.678 |
| 1344.85 | 43.888 |
| 1434.82 | 66.912 |
| 1493.92 | 62.230 |
| 1614.97 | 60.669 |
| 1679.91 | 82.130 |
| 2932.88 | 86.038 |
| 3210.13 | 92.735 |

NMR

1H-NMR of tianeptine hemi-oxalate Form A (see FIG. 6) showed that the signals of the protons near the amine moiety were shifted downfield compared to the starting material. This suggests a possible interaction between the basic nitrogen and a carboxylic moiety of the coformer. Neither the presence of the coformer nor the stoichiometry of the sample could be confirmed by 1H-NMR analysis.

1H-NMR (400 MHz, dmso-d6) δ (ppm): 1.10-1.32 (m, 4H), 1.38-1.54 (m, 4H), 2.16 (t, J=7.5 Hz, 2H), 2.40-2.58 (br band, 2H+DMSO-d6), 3.37 (s, 3H), 5.34 (s, 1H), 7.33-7.60 (m, 4H), 7.76 (br s, 2H), 7.82 (br s, 1H).

Figure 7:
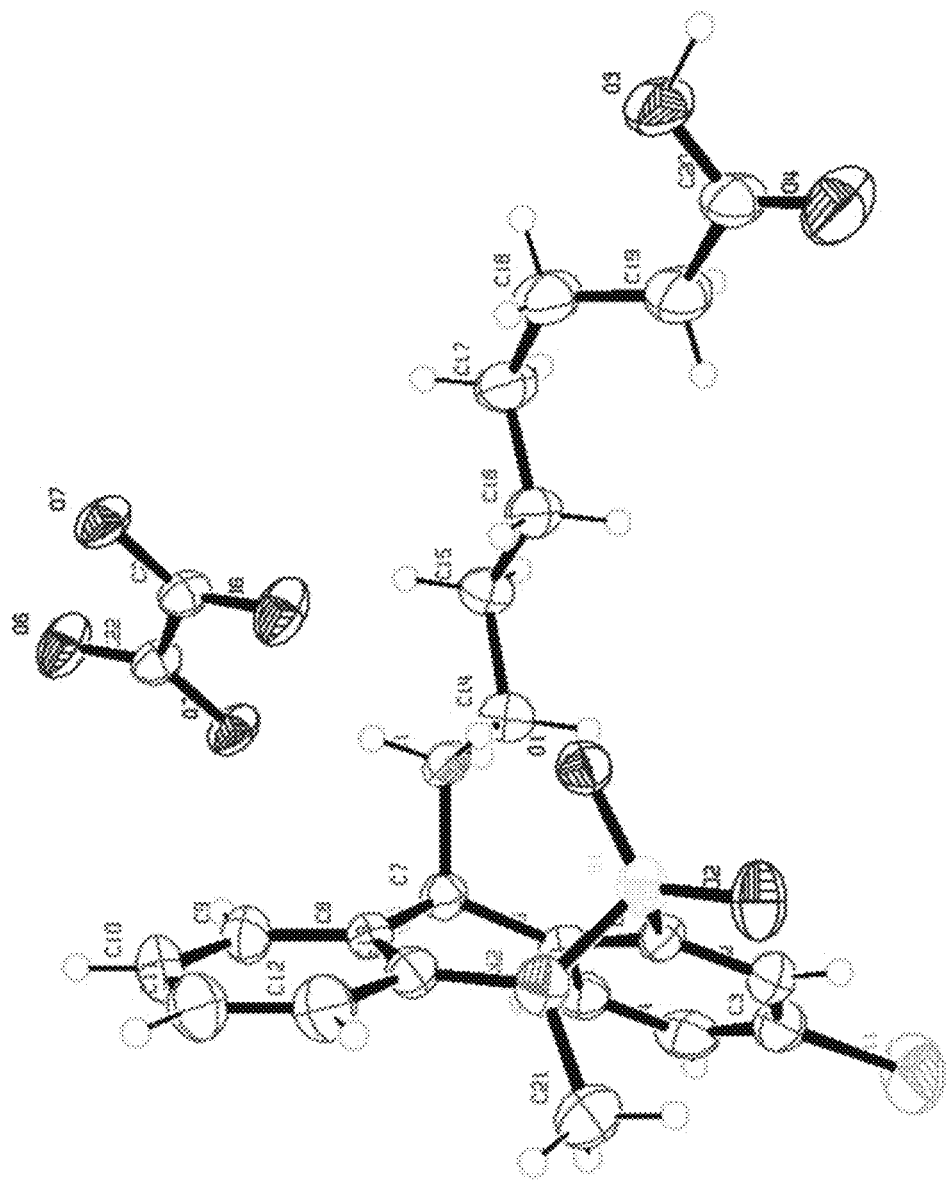
FIG. 7: Ortep drawing of the asymmetric unit with elipsoids of tianeptine hemi-oxalate (dianion).

Tianeptine hemi-oxalate Form A crystallizes as triclinic P-1 where a=9.5477(7) Å, b=11.4514(10) Å, c=11.8918(12) Å, α=113.071(9), β=94.351(7)° and γ=100.164(7)°. The asymmetric unit is made of one protonated tianeptine molecule and half molecule of oxalate (see FIG. 7). The stoichiometry of the salt is 2:1 tianeptine to oxalate meaning the oxalate is a dianion.

Figure 8:
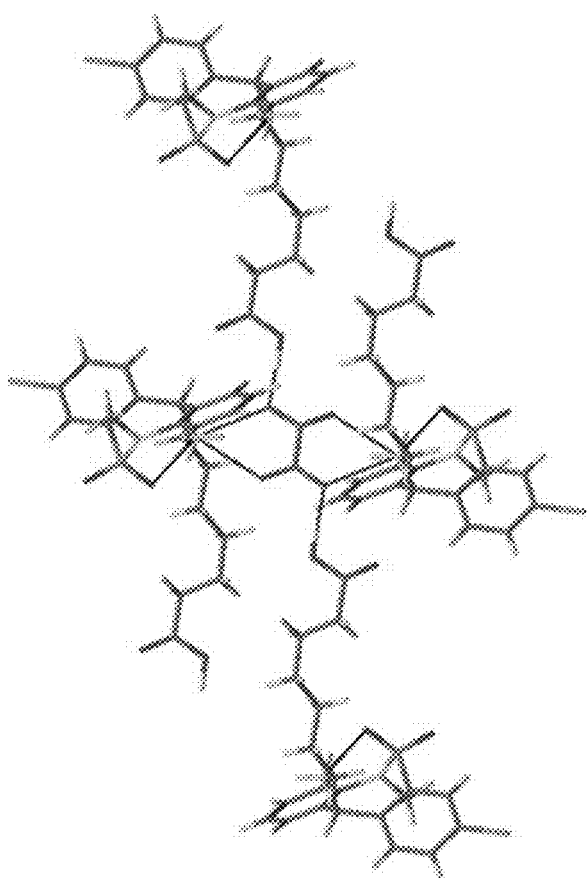
FIG. 8: Hydrogen bonds between the oxalate (central) and the four molecules of tianeptine.

The oxalate dianion forms hydrogen bonds with four different tianeptine molecules (see Table 12 and FIG. 8). The tianeptine carboxylic group interacts with the carboxylate group, while the amino group forms a bifurcated hydrogen bond with the two oxygen atoms of the oxalate as shown in FIG. 8.

TABLE 12

Hydrogen bond distances in tianeptine hemi-oxalate

| Donor-H · · · Acceptor | Distance (Å) |
|---|---|
| Intra N(1)—H(1B) . . . O(1) | 2.762(3) |
| O(3)—H(300) . . . O(7) | 2.551(4) |
| N(1)—H(1A) . . . O(7) | 2.788(3) |
| N(1)—H(1A) . . . O(6) | 2.735(3) |

TABLE 13

Atomic coordinates (×10$^4$) and equivalent isotropic displacement parameters (Å2 × 10$^3$) for tianeptine hemi-oxalate Form A

|  | x | y | Z | U(eq) |
|---|---|---|---|---|
| C(14) | 1205(3) | 6111(3) | 3786(3) | 41(1) |
| C(1) | 5009(3) | 7193(3) | 4985(3) | 34(1) |
| C(2) | 5571(4) | 7638(3) | 6220(3) | 45(1) |
| C(3) | 5203(4) | 8732(3) | 7060(3) | 53(1) |
| C(4) | 4321(4) | 9369(3) | 6677(3) | 51(1) |
| C(5) | 3757(3) | 8902(3) | 5434(3) | 42(1) |
| C(6) | 4083(3) | 7804(3) | 4558(3) | 33(1) |
| C(7) | 3349(3) | 7316(3) | 3232(3) | 34(1) |
| C(8) | 4245(3) | 7116(3) | 2186(3) | 34(1) |
| C(9) | 3644(4) | 7303(3) | 1189(3) | 50(1) |
| C(10) | 4305(4) | 7160(4) | 164(3) | 62(1) |
| C(11) | 5614(4) | 6813(4) | 118(3) | 61(1) |
| C(12) | 6235(4) | 6615(3) | 1078(3) | 51(1) |
| C(13) | 5578(3) | 6764(3) | 2120(3) | 37(1) |
| C(15) | −56(3) | 4935(3) | 3249(3) | 41(1) |
| C(16) | 351(3) | 3639(3) | 2964(3) | 45(1) |
| C(17) | −927(4) | 2490(3) | 2379(4) | 60(1) |
| C(18) | −562(5) | 1171(3) | 2010(4) | 73(1) |
| C(19) | 125(5) | 944(3) | 3033(4) | 68(1) |
| C(20) | 477(4) | −368(3) | 2746(4) | 57(1) |
| C(21) | 7782(4) | 7559(3) | 3692(4) | 58(1) |
| N(1) | 2204(2) | 6082(2) | 2887(2) | 36(1) |
| N(2) | 6413(3) | 6588(2) | 3078(2) | 41(1) |
| O(1) | 4442(2) | 4906(2) | 3091(2) | 42(1) |
| O(2) | 6693(3) | 5568(2) | 4545(2) | 57(1) |
| O(3) | −238(3) | −1283(2) | 1694(2) | 70(1) |
| O(4) | 1273(3) | −557(3) | 3438(3) | 92(1) |
| Cl(1) | 5903(2) | 9287(1) | 8610(1) | 98(1) |
| S(1) | 5633(1) | 5905(1) | 3894(1) | 40(1) |
| C(22) | −288(3) | 5635(3) | 208(3) | 34(1) |
| O(6) | −1158(2) | 5753(2) | −532(2) | 52(1) |
| O(7) | 207(2) | 6468(2) | 1306(2) | 43(1) |

U(eq) is defined as one third of the trace of the orthogonalized Uij tensor.

TABLE 14

Bond lengths [Å] and angles [°] for tianeptine hemi-oxalate Form A

| C(14)—N(1) | 1.480(4) |
|---|---|
| C(14)—C(15) | 1.519(4) |
| C(1)—C(2) | 1.379(4) |
| C(1)—C(6) | 1.399(4) |
| C(1)—S(1) | 1.773(3) |
| C(2)—C(3) | 1.386(5) |
| C(3)—C(4) | 1.366(5) |
| C(3)—Cl(1) | 1.730(3) |
| C(4)—C(5) | 1.385(5) |
| C(5)—C(6) | 1.386(4) |
| C(6)—C(7) | 1.514(4) |
| C(7)—N(1) | 1.514(3) |
| C(7)—C(8) | 1.529(4) |
| C(8)—C(9) | 1.386(4) |
| C(8)—C(13) | 1.400(4) |
| C(9)—C(10) | 1.381(5) |
| C(10)—C(11) | 1.375(5) |
| C(11)—C(12) | 1.361(5) |
| C(12)—C(13) | 1.396(4) |
| C(13)—N(2) | 1.440(4) |
| C(15)—C(16) | 1.516(4) |
| C(16)—C(17) | 1.514(4) |
| C(17)—C(18) | 1.511(5) |
| C(18)—C(19) | 1.471(5) |
| C(19)—C(20) | 1.511(5) |
| C(20)—O(4) | 1.184(4) |
| C(20)—O(3) | 1.311(4) |
| C(21)—N(2) | 1.478(4) |
| N(2)—S(1) | 1.615(3) |
| O(1)—S(1) | 1.426(2) |
| O(2)—S(1) | 1.423(2) |
| C(22)—O(6) | 1.227(3) |
| C(22)—O(7) | 1.269(3) |
| C(22)—C(22)#1 | 1.555(6) |
| N(1)—C(14)—C(15) | 111.5(2) |
| C(2)—C(1)—C(6) | 122.4(3) |
| C(2)—C(1)—S(1) | 118.2(2) |
| C(6)—C(1)—S(1) | 119.1(2) |
| C(1)—C(2)—C(3) | 118.3(3) |
| C(4)—C(3)—C(2) | 121.1(3) |
| C(4)—C(3)—Cl(1) | 120.6(3) |
| C(2)—C(3)—Cl(1) | 118.3(3) |
| C(3)—C(4)—C(5) | 119.8(3) |
| C(6)—C(5)—C(4) | 121.4(3) |
| C(5)—C(6)—C(1) | 117.1(3) |
| C(5)—C(6)—C(7) | 117.8(3) |
| C(1)—C(6)—C(7) | 125.0(2) |
| N(1)—C(7)—C(6) | 110.6(2) |
| N(1)—C(7)—C(8) | 108.5(2) |
| C(6)—C(7)—C(8) | 120.3(2) |
| C(9)—C(8)—C(13) | 117.0(3) |
| C(9)—C(8)—C(7) | 115.1(3) |
| C(13)—C(8)—C(7) | 127.8(3) |
| C(10)—C(9)—C(8) | 122.8(3) |
| C(11)—C(10)—C(9) | 119.2(4) |
| C(12)—C(11)—C(10) | 119.7(4) |
| C(11)—C(12)—C(13) | 121.5(3) |
| C(12)—C(13)—C(8) | 119.8(3) |
| C(12)—C(13)—N(2) | 114.5(3) |
| C(8)—C(13)—N(2) | 125.7(3) |
| C(16)—C(15)—C(14) | 114.7(2) |
| C(17)—C(16)—C(15) | 112.9(3) |
| C(18)—C(17)—C(16) | 114.9(3) |
| C(19)—C(18)—C(17) | 115.1(3) |
| C(18)—C(19)—C(20) | 118.3(3) |
| O(4)—C(20)—O(3) | 123.6(3) |
| O(4)—C(20)—C(19) | 122.8(3) |
| O(3)—C(20)—C(19) | 113.5(3) |
| C(14)—N(1)—C(7) | 116.0(2) |
| C(13)—N(2)—C(21) | 116.4(3) |
| C(13)—N(2)—S(1) | 120.6(2) |
| C(21)—N(2)—S(1) | 116.4(2) |
| O(2)—S(1)—O(1) | 118.86(14) |
| O(2)—S(1)—N(2) | 108.81(14) |
| O(1)—S(1)—N(2) | 107.18(13) |
| C(9)—C(8)—C(13) | 117.0(3) |
| C(9)—C(8)—C(7) | 115.1(3) |
| C(13)—C(8)—C(7) | 127.8(3) |
| C(10)—C(9)—C(8) | 122.8(3) |
| C(11)—C(10)—C(9) | 119.2(4) |
| C(12)—C(11)—C(10) | 119.7(4) |
| C(11)—C(12)—C(13) | 121.5(3) |
| C(12)—C(13)—C(8) | 119.8(3) |
| C(12)—C(13)—N(2) | 114.5(3) |
| C(8)—C(13)—N(2) | 125.7(3) |
| C(16)—C(15)—C(14) | 114.7(2) |
| C(17)—C(16)—C(15) | 112.9(3) |
| C(18)—C(17)—C(16) | 114.9(3) |
| C(19)—C(18)—C(17) | 115.1(3) |
| C(18)—C(19)—C(20) | 118.3(3) |
| O(4)—C(20)—O(3) | 123.6(3) |
| O(4)—C(20)—C(19) | 122.8(3) |
| O(3)—C(20)—C(19) | 113.5(3) |
| C(14)—N(1)—C(7) | 116.0(2) |
| C(13)—N(2)—C(21) | 116.4(3) |
| C(13)—N(2)—S(1) | 120.6(2) |

TABLE 14-continued

Bond lengths [Å] and angles [°]
for tianeptine hemi-oxalate Form A

| | |
|---|---|
| C(21)—N(2)—S(1) | 116.4(2) |
| O(2)—S(1)—O(1) | 118.86(14) |
| O(2)—S(1)—N(2) | 108.81(14) |
| O(1)—S(1)—N(2) | 107.18(13) |
| C(13)—N(2)—S(1) | 120.6(2) |
| C(21)—N(2)—S(1) | 116.4(2) |
| O(2)—S(1)—O(1) | 118.86(14) |
| O(2)—S(1)—N(2) | 108.81(14) |
| O(1)—S(1)—N(2) | 107.18(13) |
| O(2)—S(1)—C(1) | 108.21(14) |
| O(1)—S(1)—C(1) | 110.17(13) |
| N(2)—S(1)—C(1) | 102.35(14) |
| O(6)—C(22)—O(7) | 125.7(3) |
| O(6)—C(22)—C(22)#1 | 118.6(3) |
| O(7)—C(22)—C(22)#1 | 115.6(3) |

Solubility

The solubility of the tianeptine hemi-oxalate form A was compared with that of the tianeptine sodium salt at various pH using standard buffers as shown in Table 15 below.

TABLE 15

Solubility Comparison

| Medium | Prepared according to | Tianeptine Hemi-Oxalate Form A solubility (mg/ml) | Tianeptine Sodium solubility (mg/ml) |
|---|---|---|---|
| pH 1.2 | USP | 0.702 | 4.645 |
| pH 4.5 (Phosphate) | USP | 0.313 | 2.101 |
| pH 4.5 (Acetate) | PhEu | 0.317 | 3.676 |
| pH 6.8 (Phosphate) | USP | 0.585 | 1.768 |
| Water | 20 mg in 100 ml | Soluble after 40 minutes of mixing with magnetic stirrer | Freely Soluble |

Hygroscopicity

The hygroscopicity of the tianeptine hemi-oxalate Form A was compared that of the tianeptine sodium salt. Crystals of the tianeptine samples were observed in open air or in closed conditions (crimped glass vial) under varying temperature and relative humidity (RH) parameters as shown in Tables 16-17 below. Hygroscopicity was measured as the percentage (%) of water in the sample using the Karl Fisher (KF) method at day 1, 3, and 7. While tianeptine sodium is extremely hygroscopic (Table 17), the water content of the tianeptine hemi-oxalate salt was practically unchanged after 7 days, in open air or in a crimped glass vial (Table 16).

TABLE 16

Hygroscopicity of Tianeptine hemi-oxalate Form A

| Tianeptine Hemi-Oxalate Form A | Time 0 | Time 1 day | | Time 3 days | | Time 7 days | |
|---|---|---|---|---|---|---|---|
| | | Open Air | Crimped glass vial | Open Air | Crimped glass vial | Open Air | Crimped glass vial |
| Storage Conditions | 0.47% | | | | | | |
| 25° C., 60% RH | | 0.35% | 0.34% | 0.28% | 0.18% | 0.22% | 0.28% |
| 30° C., 65% RH | | 0.28% | 0.27% | 0.18% | 0.16% | 0.30% | 0.30% |
| 40° C., 75% RH | | 0.06% | 0.30% | 0.30% | 0.16% | 0.17% | 0.20% |

TABLE 17

Hygroscopicity of Tianeptine Sodium

| Tianeptine Sodium | Time 0 | Time 1 day | | Time 3 days | | Time 7 days | |
|---|---|---|---|---|---|---|---|
| | | Open Air | Crimped glass vial | Open Air | Crimped glass vial | Open Air | Crimped glass vial |
| Storage Conditions | 3.09% | | | | | | |
| 25° C., 60% RH | | 13.86% | 2.94% | NP | 2.42% | NP | 2.56% |
| 30° C., 65% RH | | 14.80% | 2.63% | NP | 2.65% | NP | 2.77% |
| 40° C., 75% RH | | 16.22% | 2.84% | NP | 2.73% | NP | 2.53% |

NP = Not performed due to visual decomposition of the extremely hygroscopic sample at day 1.

Example 2

Tianeptine Hemi-Oxalate and Mono-Oxalate Form A Mixture

The above reaction was repeated at a smaller scale to confirm the formation of the new species. 10-100 g of tianeptine free base was dissolved in 200-2000 mL of acetone and the solution was heated at reflux. 2-20 g (1 eq.) of oxalic acid were added to the clear solution and the resulting mixture was stirred at 40-60° C. for 30-60 minutes. The coformer was instantly solubilized and a clear solution was observed. After a few minutes, the formation of a white precipitate was observed. The mixture was then cooled at room temperature and stirred for 12-24 hours. The white precipitate was recovered under vacuum, washed with acetone and dried at 40-60° C. for 12-24 hours.

Replication of the reaction confirmed the presence of tianeptine mono-oxalate Form A in mixture with hemi-oxalate Form A. Such mixtures could also be obtained by mixing the two independently prepared species.

DSC analysis of the mixture showed two distinct endothermic peaks. The first endothermic peak at 176° C. (onset at 174.64° C.) and the second endothermic peak was detected at 200° C. (onset 195.45° C.), which was imputable to the melting and decomposition of the tianeptine hemi-oxalate Form A. TG analysis confirmed that the sample was dried and that the decomposition occurred below 17° C. in two distinct events where approximately 12% and 9% of weight was lost.

Melting point analysis of the mixture highlighted that the first event observed during the DSC analysis was ascribable to the melting of the sample without its decomposition (as visible at 166, 178 and 188° C.). The second endothermic event started with the melting of the sample followed by decomposition.

Interconversion Slurry Tests

The mixture was subjected to slurry experiments to evaluate potential conversion between the two salts. 100 mg was suspended in 2 mL of a single solvent and left under magnetic stirring at approximately 200 rpm at room temperature for 3 and 7 days as well as at 50° C. for 3 days. Afterwards, the samples were checked by XRPD analyses and the resulting diffractograms were compared to the XRPD patterns of the starting material and that of tianeptine hemi-oxalate Form A. The results of the slurry experiments are shown in Table 18.

TABLE 18

Results of the slurry experiments

| Solvent | Slurry-3 days-RT | Slurry-7 days-RT | Slurry-50° C.-3 days |
|---|---|---|---|
| Acetone | tianeptine hemi-oxalate Form A + tianeptine mono-oxalate Form A | tianeptine hemi-oxalate Form A + tianeptine mono-oxalate Form A | tianeptine hemi-oxalate Form A |
| Ethyl Acetate | tianeptine hemi-oxalate Form A + tianeptine mono-oxalate Form A | tianeptine hemi-oxalate Form A + tianeptine mono-oxalate Form A | tianeptine hemi-oxalate Form A + tianeptine mono-oxalate Form A |

Stability of Tianeptine Hemi-Oxalate Salt

These analyses confirmed that tianeptine hemi-oxalate Form A is the most thermodynamically stable form due to its higher melting point and stability during slurry experiments. To assess the phase stability of the tianeptine hemi-oxalate Form A, several slurry experiments were performed in different solvents or solvent mixtures and different temperature conditions. No significant modifications in the XRPD pattern were observed after the tests. In addition, stability tests were carried out in different conditions of temperature (25-60° C.) and relative humidity (0-75% C). In all the tested conditions, the crystal form did not Grinding and water kneading experiments were conducted as well and they did not induce a phase shift. Based on the slurry experiments and stability tests performed Tianeptine hemi-oxalate Form A can be considered the thermodynamic stable form.

When the reaction ratio between tianeptine and oxalic acid was 2:1, the formation of tianeptine hemi-oxalate Form A was preferred, whereas when the ratio was 1:1 in some low polar solvents, the formation of tianeptine mono-oxalate Form A was favored.

Example 3

Tianeptine Mono-Oxalate Form A

The following synthetic methodology was used to prepare tianeptine mono-oxalate Form A. 2-20 g of tianeptine was dissolved in 200-2000 mL of ethyl acetate under magnetic stirring at 40-60° C. After 15-30 minutes, the hot clear solution was cooled to room temperature and left under stirring for 90-180 minutes, but the solution remained clear. 1-10 g of oxalic acid was dissolved in 20-200 mL of ethyl acetate at room temperature, obtaining a clear solution (concentration=50 mg/mL). 8-80 mL of the oxalic acid solution (1 eq.) was then added rapidly to the tianeptine solution under magnetic stirring at room temperature. A white powder instantly precipitated. After 60-90 minutes, the suspension was recovered under vacuum, washed with ethyl acetate, and dried under vacuum ($10^{-2}$ atm) at room temperature overnight.

The XRPD diffraction pattern and its peak list for tianeptine mono-oxalate Form A are illustrated in FIG. 10 and Table 19, respectively. The FT-IR spectrum for tianeptine mono-oxalate Form A is reported in FIG. 11 and its peak list is reported in Table 20.

TABLE 19

XRPD Peaks List of Tianeptine mono-Oxalate Form A

| Pos. [°2Th.] | Height [cts] | FWHM [°2Th.] | d-spacing [Å] | Rel. Int. [%] |
|---|---|---|---|---|
| 5.7082 | 63.61 | 0.8029 | 15.48295 | 2.10 |
| 7.4941 | 709.24 | 0.1171 | 11.79669 | 23.46 |
| 8.2794 | 645.85 | 0.1171 | 10.67947 | 21.36 |
| 10.1224 | 3023.10 | 0.1338 | 8.73884 | 100.00 |
| 10.4738 | 2158.15 | 0.1338 | 8.44637 | 71.39 |
| 11.9311 | 1022.01 | 0.1171 | 7.41780 | 33.81 |
| 14.7375 | 1181.20 | 0.1171 | 6.01097 | 39.07 |
| 16.2068 | 732.25 | 0.0669 | 5.46918 | 24.22 |
| 16.3175 | 775.67 | 0.0836 | 5.43235 | 25.66 |
| 17.0803 | 441.14 | 0.1673 | 5.19140 | 14.59 |
| 17.9805 | 1507.42 | 0.1673 | 4.93348 | 49.86 |
| 18.1409 | 907.54 | 0.0836 | 4.89022 | 30.02 |
| 18.6654 | 1066.16 | 0.1506 | 4.75396 | 35.27 |
| 19.2422 | 130.86 | 0.1338 | 4.61275 | 4.33 |
| 19.8272 | 160.52 | 0.2007 | 4.47796 | 5.31 |
| 20.9993 | 2021.18 | 0.1840 | 4.23059 | 66.86 |
| 21.6871 | 986.74 | 0.1673 | 4.09795 | 32.64 |
| 22.0789 | 1127.40 | 0.2007 | 4.02611 | 37.29 |
| 22.7397 | 1599.50 | 0.0669 | 3.91058 | 52.91 |
| 22.9548 | 1145.78 | 0.1004 | 3.87441 | 37.90 |
| 23.3796 | 1431.11 | 0.1673 | 3.80498 | 47.34 |
| 23.9564 | 741.27 | 0.1428 | 3.71157 | 24.52 |
| 24.0542 | 767.99 | 0.0816 | 3.70589 | 25.40 |
| 24.9620 | 622.68 | 0.1224 | 3.56429 | 20.60 |

TABLE 19-continued

XRPD Peaks List of Tianeptine mono-Oxalate Form A

| Pos. [°2Th.] | Height [cts] | FWHM [°2Th.] | d-spacing [Å] | Rel. Int. [%] |
|---|---|---|---|---|
| 25.4332 | 493.19 | 0.0816 | 3.49931 | 16.31 |
| 25.8455 | 120.08 | 0.1224 | 3.44442 | 3.97 |
| 27.1812 | 272.70 | 0.1224 | 3.27811 | 9.02 |
| 28.2343 | 273.69 | 0.2856 | 3.15819 | 9.05 |
| 28.7192 | 564.65 | 0.1632 | 3.10596 | 18.68 |
| 29.8322 | 823.17 | 0.1428 | 2.99257 | 27.23 |
| 30.7901 | 374.48 | 0.1224 | 2.90161 | 12.39 |
| 31.8007 | 237.28 | 0.2856 | 2.81167 | 7.85 |
| 32.5020 | 239.28 | 0.1428 | 2.75258 | 7.91 |
| 33.7079 | 166.14 | 0.2040 | 2.65681 | 5.50 |
| 34.6256 | 49.87 | 0.2448 | 2.58847 | 1.65 |
| 35.1208 | 141.34 | 0.2448 | 2.55310 | 4.68 |
| 36.2371 | 158.16 | 0.2040 | 2.47697 | 5.23 |
| 36.5029 | 184.56 | 0.2448 | 2.45954 | 6.11 |
| 37.0868 | 179.15 | 0.3672 | 2.42215 | 5.93 |
| 38.2112 | 90.60 | 0.2448 | 2.35342 | 3.00 |
| 38.9995 | 95.43 | 0.4896 | 2.30765 | 3.16 |
| 39.7161 | 60.60 | 0.2448 | 2.26765 | 2.00 |

TABLE 20

FT-IR Peak List of Tianeptine mono-Oxalate Form A.

| Position (cm−1) | Intensity [% T] |
|---|---|
| 407 | 78.015 |
| 420 | 69.840 |
| 437 | 49.006 |
| 472 | 60.639 |
| 503 | 66.437 |
| 542 | 38.170 |
| 574 | 14.288 |
| 590 | 25.372 |
| 599 | 45.604 |
| 634 | 87.938 |
| 672 | 51.844 |
| 698 | 48.676 |
| 715 | 46.116 |
| 730 | 63.379 |
| 745 | 58.880 |
| 756 | 51.876 |
| 765 | 38.000 |
| 817 | 58.594 |
| 848 | 59.972 |
| 881 | 67.940 |
| 895 | 69.758 |
| 915 | 46.973 |
| 956 | 85.792 |
| 1012 | 82.832 |
| 1044 | 57.782 |
| 1058 | 61.391 |
| 1068 | 73.339 |
| 1103 | 53.620 |
| 1140 | 54.137 |
| 1162 | 39.190 |
| 1183 | 39.124 |
| 1206 | 58.980 |
| 1218 | 61.413 |
| 1241 | 35.677 |
| 1291 | 50.234 |
| 1319 | 66.721 |
| 1347 | 38.293 |
| 1393 | 55.381 |
| 1445 | 69.191 |
| 1459 | 74.454 |
| 1474 | 67.558 |
| 1500 | 73.813 |
| 1578 | 59.760 |
| 1623 | 44.368 |
| 1724 | 51.663 |
| 1763 | 57.945 |
| 2162 | 98.026 |
| 2324 | 93.872 |
| 2495 | 91.427 |
| 2633 | 89.069 |
| 2862 | 87.030 |
| 2932 | 84.185 |
| 3098 | 91.653 |
| 3177 | 86.700 |
| 3245 | 89.155 |

Figure 12:
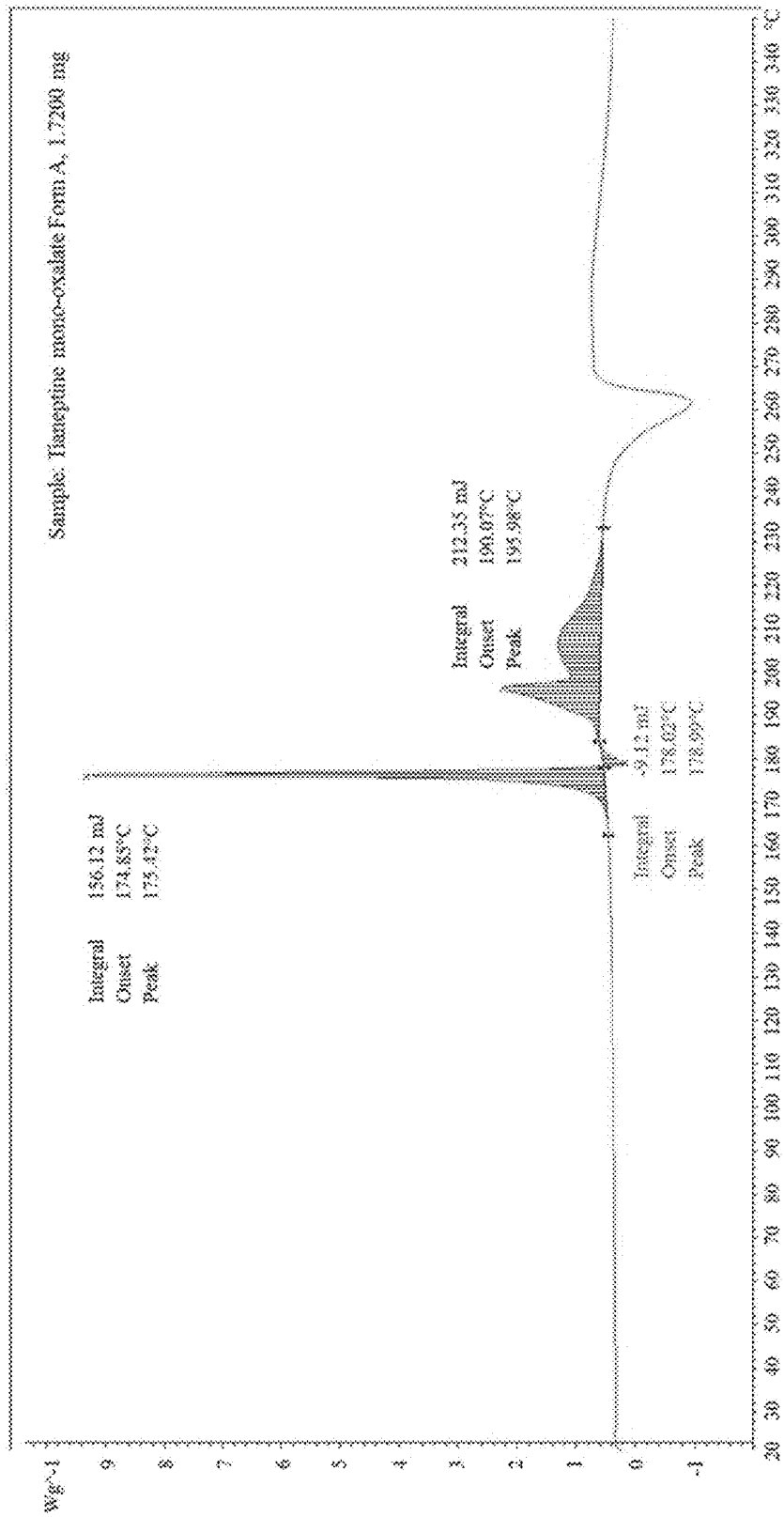
FIG. 12: DSC profile of tianeptine mono-oxalate Form A.

The DSC profile reported in FIG. 12 showed a sharp endothermic peak at 175° C. (onset 174.8° C.), which was associated with the melting of the sample. It also showed an exothermic peak at 179° C. associated to recrystallization of the sample. Two endothermic events were also observed at 196° C. These peaks were associated with the melting of tianeptine mono-oxalate Form A while the broad peak was due to the decomposition of the oxalic acid.

Figure 13:
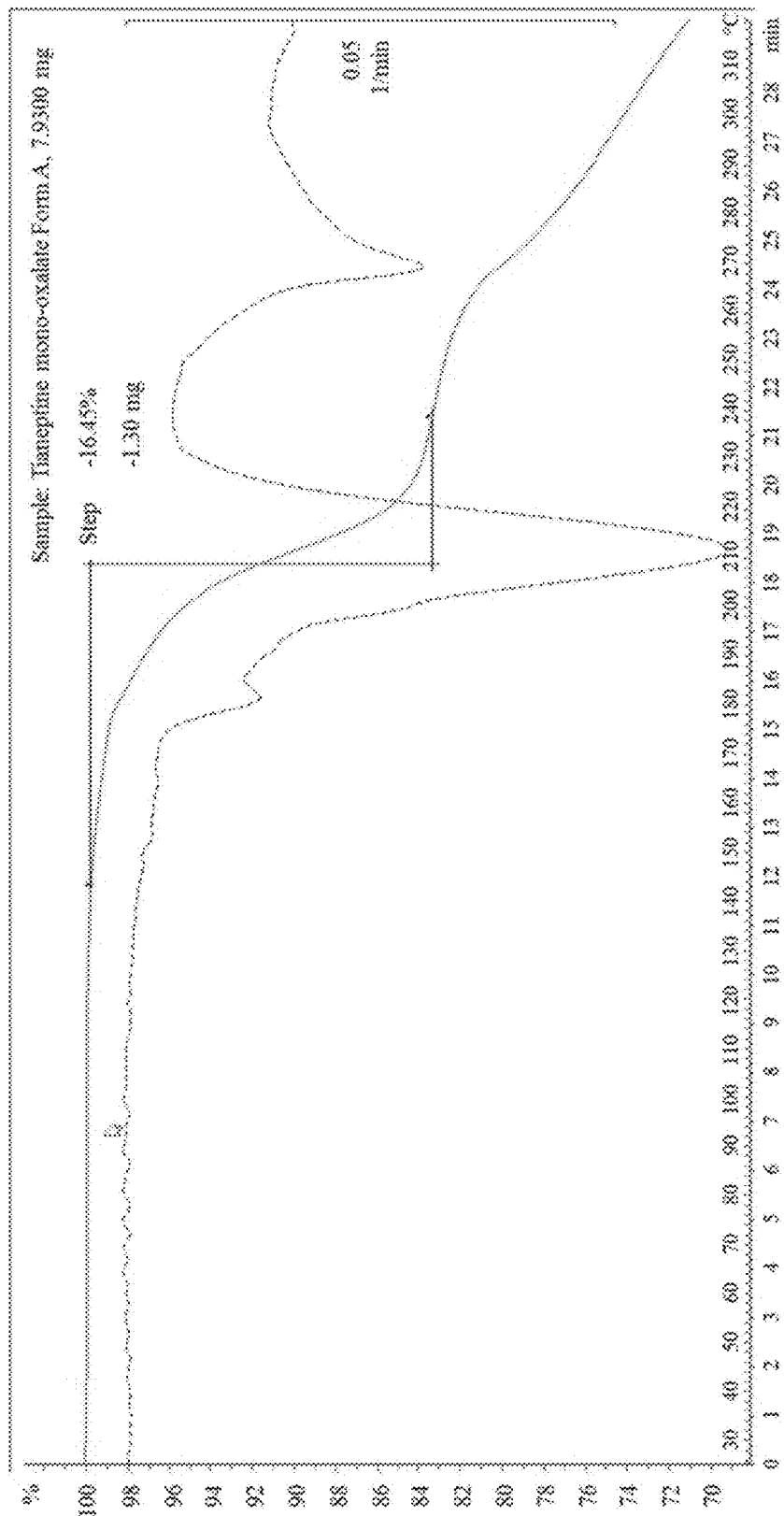
FIG. 13: TGA profile of tianeptine mono-oxalate Form A.

The TGA profile reported in FIG. 13 only showed the degradation of the sample during the thermal events seen in the DSC profile. The weight loss caused by the decomposition of the oxalic acid in $CO_2$ WAS 16.4%

Tianeptine mono-oxalate Form A was anhydrous, slightly hygroscopic and started to convert into tianeptine hemi-oxalate Form A at 40-60° C. under high humidity (75% RH) and by water kneading. It appeared stable if it was milled without water and if it was stored in milder conditions (25° C. and 60-75% RH) or at high temperatures (40-60° C.) without humidity (RH≈0%).

No significant difference in the water solubility at room temperature was visually observed between the two forms (lower than 1 mg/mL).

Example 4

Tianeptine Mono-Oxalate Form B

To prepare tianeptine mono-oxalate Form B, 50 mg of tianeptine free base was dissolved in 6.0 mL of nitromethane. 10 mg (1 equivalent) of oxalic acid was dissolved in 0.5 mL of nitromethane and the resulting solution was added to the solution of tianeptine. Immediately after the addition, the reaction mixture was cooled in an ice bath. After approximately 7 minutes, the white precipitate was recovered under vacuum and analyzed by XRPD.

The diffractogram and corresponding peak list of tianeptine mono-oxalate Form B are reported in FIG. 14 and Table 21. The FT-IR spectrum of tianeptine mono-oxalate Form B is reported in FIG. 15 and its peak list is reported in Table 22.

TABLE 21

XRPD Peaks List of Tianeptine mono-Oxalate Form B

| Pos. [°2Th.] | Height [cts] | FWHM [°2Th.] | d-spacing [Å] | Rel. Int. [%] |
|---|---|---|---|---|
| 5.9877 | 53.99 | 0.2007 | 14.76081 | 2.46 |
| 7.4484 | 644.86 | 0.1171 | 11.86894 | 29.42 |
| 7.8000 | 332.97 | 0.1171 | 11.33473 | 15.19 |
| 8.6132 | 2191.71 | 0.1506 | 10.26635 | 100.00 |
| 10.4137 | 1467.04 | 0.1338 | 8.49500 | 66.94 |
| 10.7756 | 561.19 | 0.1171 | 8.21054 | 25.61 |
| 12.0662 | 111.82 | 0.1338 | 7.33509 | 5.10 |
| 13.6920 | 257.13 | 0.0836 | 6.46751 | 11.73 |

TABLE 21-continued

XRPD Peaks List of Tianeptine mono-Oxalate Form B

| Pos. [°2Th.] | Height [cts] | FWHM [°2Th.] | d-spacing [Å] | Rel. Int. [%] |
|---|---|---|---|---|
| 14.8560 | 875.54 | 0.1840 | 5.96332 | 39.95 |
| 15.5731 | 811.65 | 0.1338 | 5.69028 | 37.03 |
| 16.0391 | 451.42 | 0.1506 | 5.52600 | 20.60 |
| 17.4715 | 795.13 | 0.1338 | 5.07603 | 36.28 |
| 17.8589 | 167.53 | 0.1338 | 4.96679 | 7.64 |
| 18.8422 | 163.02 | 0.1004 | 4.70975 | 7.44 |
| 19.2387 | 206.33 | 0.1338 | 4.61359 | 9.41 |
| 19.8786 | 562.24 | 0.1338 | 4.46648 | 25.65 |
| 20.2416 | 478.57 | 0.1004 | 4.38719 | 21.84 |
| 20.4483 | 579.19 | 0.1338 | 4.34331 | 26.43 |
| 20.9058 | 684.79 | 0.1171 | 4.24929 | 31.24 |
| 21.2650 | 622.71 | 0.1338 | 4.17831 | 28.41 |
| 21.6364 | 453.54 | 0.1338 | 4.10743 | 20.69 |
| 21.9569 | 437.70 | 0.1171 | 4.04820 | 19.97 |
| 22.7958 | 225.10 | 0.0669 | 3.90109 | 10.27 |
| 23.4708 | 1586.21 | 0.1506 | 3.79039 | 72.37 |
| 23.7824 | 397.64 | 0.1338 | 3.74144 | 18.14 |
| 24.3598 | 833.23 | 0.1506 | 3.65404 | 38.02 |
| 24.6971 | 1117.13 | 0.1506 | 3.60489 | 50.97 |
| 25.2005 | 227.05 | 0.1506 | 3.53402 | 10.36 |
| 25.7272 | 95.62 | 0.1338 | 3.46284 | 4.36 |
| 26.7623 | 64.66 | 0.1673 | 3.33121 | 2.95 |
| 27.3979 | 469.15 | 0.1171 | 3.25537 | 21.41 |
| 27.6142 | 248.09 | 0.1004 | 3.23036 | 11.32 |
| 29.0818 | 182.64 | 0.1004 | 3.07059 | 8.33 |
| 29.5176 | 62.93 | 0.1004 | 3.02624 | 2.87 |
| 30.1255 | 254.64 | 0.1506 | 2.96655 | 11.62 |
| 30.4403 | 205.52 | 0.1004 | 2.93658 | 9.38 |
| 30.8331 | 56.14 | 0.1338 | 2.90006 | 2.56 |
| 31.3986 | 69.24 | 0.1338 | 2.84911 | 3.16 |
| 31.7911 | 85.16 | 0.2007 | 2.81483 | 3.89 |
| 32.3064 | 438.17 | 0.1224 | 2.76880 | 19.99 |
| 32.4065 | 443.19 | 0.0816 | 2.76733 | 20.22 |
| 33.1884 | 54.59 | 0.1632 | 2.69721 | 2.49 |
| 33.8013 | 48.48 | 0.1632 | 2.64969 | 2.21 |
| 34.5438 | 170.40 | 0.1020 | 2.59441 | 7.77 |
| 35.4188 | 36.28 | 0.2448 | 2.53230 | 1.66 |
| 35.8785 | 69.62 | 0.1224 | 2.50091 | 3.18 |
| 36.2912 | 126.50 | 0.2040 | 2.47341 | 5.77 |
| 37.2195 | 37.44 | 0.2448 | 2.41382 | 1.71 |
| 38.2239 | 25.23 | 0.2856 | 2.35267 | 1.15 |
| 39.0687 | 83.00 | 0.2040 | 2.30372 | 3.79 |

TABLE 22

FT-IR Peak List of Tianeptine mono-Oxalate Form B

| Position (cm−1) | Intensity [% T] |
|---|---|
| 417 | 80.583 |
| 433 | 60.709 |
| 470 | 61.112 |
| 490 | 73.589 |
| 506 | 74.658 |
| 542 | 44.891 |
| 573 | 33.138 |
| 588 | 34.548 |
| 598 | 45.975 |
| 636 | 88.682 |
| 672 | 64.770 |
| 697 | 62.702 |
| 718 | 53.966 |
| 726 | 58.476 |
| 743 | 69.288 |
| 754 | 66.477 |
| 767 | 56.363 |
| 806 | 74.846 |
| 817 | 74.210 |
| 842 | 71.115 |
| 858 | 71.329 |
| 892 | 75.547 |
| 913 | 60.377 |
| 1009 | 87.441 |
| 1043 | 64.997 |
| 1053 | 74.675 |
| 1066 | 76.779 |
| 1107 | 63.129 |
| 1140 | 60.337 |
| 1181 | 44.309 |
| 1217 | 50.155 |
| 1240 | 43.325 |
| 1289 | 69.256 |
| 1355 | 58.928 |
| 1407 | 72.611 |
| 1445 | 80.501 |
| 1474 | 80.926 |
| 1495 | 79.647 |
| 1575 | 71.109 |
| 1618 | 58.270 |
| 1716 | 60.858 |
| 1755 | 70.768 |
| 2324 | 96.331 |
| 2859 | 88.179 |
| 2932 | 85.760 |
| 3178 | 90.209 |

Figure 16:
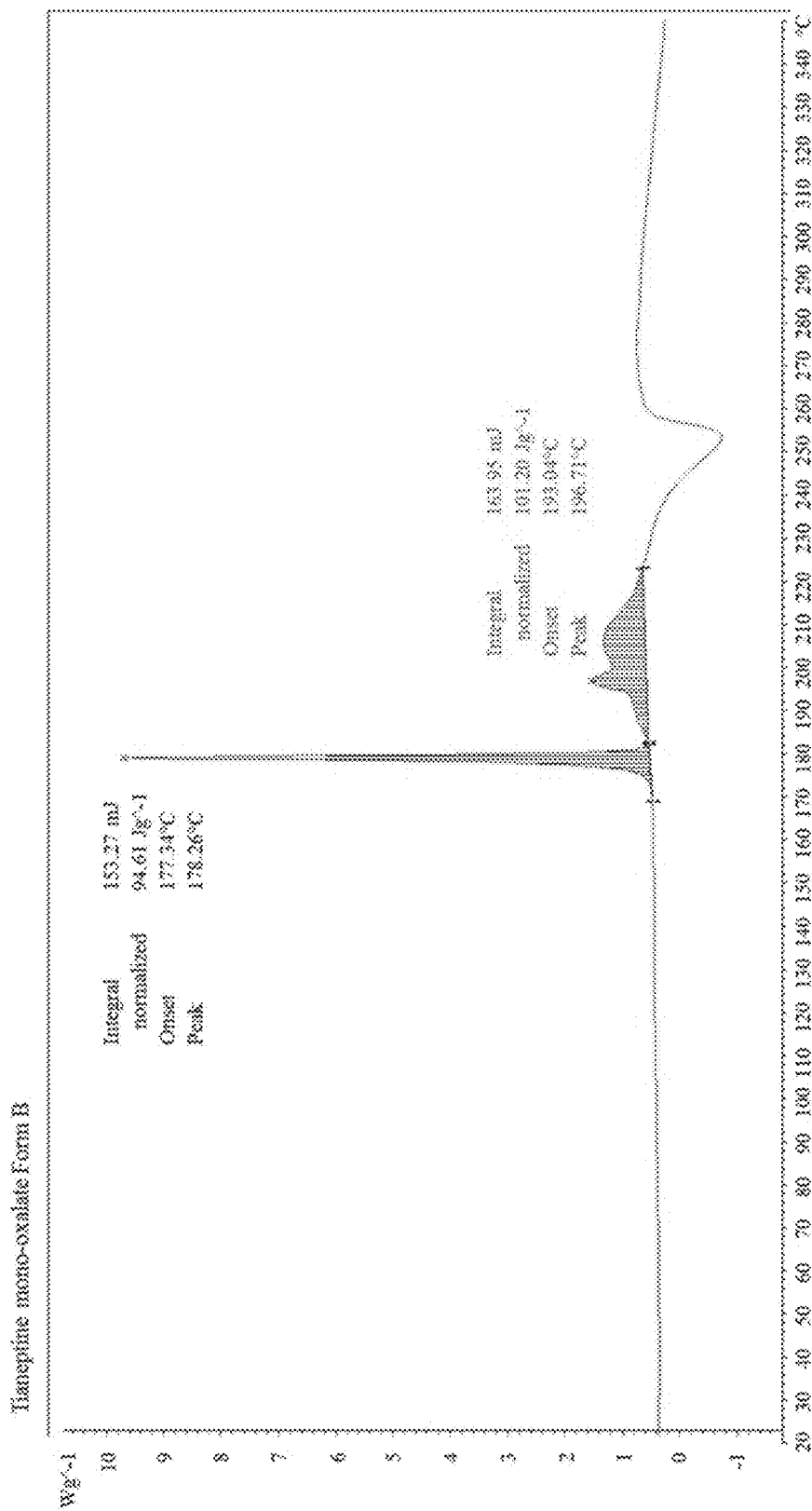
FIG. 16: DSC profile of tianeptine mono-oxalate Form B.

The DSC profile (FIG. 16) shows a sharp endothermic peak at 178° C. (onset 177.3° C.), which was associated with the sample melting. It also showed two endothermic events that took place at 197° C. These events were probably associated with the melting of tianeptine mono-oxalate while the broad peak was due to the decomposition of the oxalic acid.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and devices within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods or devices, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict any definitions in this disclosure.

What is claimed is:

1. A pharmaceutical composition comprising an anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide (anhydrous crystalline tianeptine hemi-oxalate salt) and a pharmaceutically acceptable carrier or excipient, wherein the anhydrous crystalline tianeptine hemi-oxalate salt is characterized by an X-ray diffraction pattern (XRPD) comprising at least one peak selected from the group consisting of 8.2, 8.6, 9.1, and 9.5 degrees 2θ±0.3 degrees 2θ.

2. The pharmaceutical composition of claim 1, wherein the XRPD pattern further comprises at least one peak selected from the group consisting of 11.5, 14.2, 15.2, 15.8, 16.4, 19.2, 22.1, 23.9, 26.9, and 27.4 degrees 2θ±0.3 degrees 2θ.

3. The pharmaceutical composition of claim 1, wherein the pharmaceutical composition is in a solid form, a suspension form, or a liquid form.

4. A pharmaceutical composition comprising an anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide (anhydrous crystalline tianeptine mono-oxalate salt) and a pharmaceutically acceptable carrier or excipient, wherein the anhydrous crystalline tianeptine mono-oxalate salt is characterized by an X-ray diffraction pattern (XRPD) comprising at least one peak selected from the group consisting of 10.1 and 10.5 degrees 2θ±0.3 degrees 2θ.

5. The pharmaceutical composition of claim 4, wherein the XRPD pattern further comprises at least one peak selected from the group consisting of 7.5, 8.3, 11.9, 14.7, 16.2, 17.9, 18.7, 21.0, 21.7, and 22.1 degrees 2θ±0.3 degrees 2θ.

6. The pharmaceutical composition of claim 4, wherein the pharmaceutical composition is in a solid form, a suspension form, or a liquid form.

7. A pharmaceutical composition comprising a mixture of an anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide and an anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide, and a pharmaceutically acceptable carrier or excipient, wherein the mixture is characterized by an XRPD pattern comprising at least one peak selected from the group consisting of 10.1, 10.5, 15.8, and 19.2 degrees 2θ±0.3 degrees 2θ.

8. The pharmaceutical composition of claim 7, wherein the XRPD pattern further comprises at least one additional peak selected from the group consisting of 7.5, 8.3, 11.5, 11.9, 14.2, 14.7, 15.2, 16.2, 16.3, 16.4, 17.9, 18.7, 21.0, 21.7, 22.1, 23.9, 26.9, and 27.4 degrees 2θ±0.3 degrees 2θ.

9. The pharmaceutical composition of claim 7, wherein the pharmaceutical composition is in a solid form, a suspension form, or a liquid form.

10. The pharmaceutical composition of any one of claims 1, 4, and 7, wherein the pharmaceutical composition is in an extended release form.

11. The pharmaceutical composition of claim 10, wherein the extended release form is a sustained release form, a controlled release form, or a delayed release form.

12. The pharmaceutical composition of any one of claims 1, 4, and 7, wherein the pharmaceutical composition is formulated for once daily administration.

13. The pharmaceutical composition of any one of claims 1, 4, and 7, wherein the pharmaceutical composition is suitable for oral administration.

14. The pharmaceutical composition of any one of claims 1, 4, and 7, wherein the pharmaceutical composition is osmotically active.

15. A pharmaceutical composition comprising two or more layers, each layer comprising one or more of:
(a) an anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide (anhydrous crystalline tianeptine hemi-oxalate salt), wherein the anhydrous crystalline tianeptine hemi-oxalate salt is characterized by an X-ray diffraction pattern (XRPD) comprising at least one peak selected from the group consisting of 8.2, 8.6, 9.1, and 9.5 degrees 2θ±0.3 degrees 2θ;
(b) an anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide (anhydrous crystalline tianeptine mono-oxalate salt), wherein the anhydrous crystalline tianeptine mono-oxalate salt is characterized by an X-ray diffraction pattern (XRPD) comprising at least one peak selected from the group consisting of 10.1 and 10.5 degrees 2θ±0.3 degrees 2θ; or
(c) a mixture of (a) and (b);
wherein one layer is substantially released prior to the substantial release of another layer in vivo.

16. A method of treating: (a) a psychiatric disorder induced by corticosteroid treatment, (b) asthma, or (c) chronic obstructive pulmonary disorder, in a subject in need thereof, comprising administering to the subject the pharmaceutical composition of any one of claims 1, 4, 7, and 15.

17. A method of producing an anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide, said method comprising the following steps:
(a) preparing a mixture of (RS)-7-(3-chloro-6-methyl-6,11-dihydrodibenzo[c,f] [1,2]thiazepin-11-ylamino)heptanoic acid S,S-dioxide free base and oxalic acid in acetone;
(b) heating the mixture of step (a) to about 40° C. 60° C. to afford a solution;
(c) cooling the solution of step (b) to about 25° C. to form a precipitate comprising the anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide; and
(d) recovering the precipitate of step (c) to afford the anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide.

18. A method of producing a mixture of an anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide and an anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide, said method comprising the following steps:
(a) dissolving (RS)-7-(3-chloro-6-methyl-6,11-dihydrodibenzo[c,f] [1,2]thiazepin-11-ylamino)heptanoic acid S,S-dioxide free base in acetone to afford solution A;
(b) heating solution A to reflux;
(c) adding oxalic acid to the refluxing solution A of step (b) to afford solution B;
(d) cooling solution B to about 40° C. 60° C. to form a precipitate comprising the mixture of the anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide and the anhydrous crystalline mono-oxalate salt of (RS)-7-(3-chloro-6- methyl-6,11-dihydrodibenzo[c,f] [1,2]thiazepin-11-ylamino)heptanoic acid S,S-dioxide; and
(e) recovering the precipitate of step (d) to afford the mixture of the anhydrous crystalline hemi-oxalate salt of (RS)-7-(3-chloro-6-methyl-6,11-dihydrodibenzo[c,f] [1,2]thiazepin-11-ylamino)heptanoic acid S,S-dioxide and the anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide.

19. A method of producing an anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide, said method comprising the following steps:
(a) dissolving (RS)-7-(3-chloro-6-methyl-6,11-dihydrodibenzo[c,f] [1,2]thiazepin-11-ylamino)heptanoic acid S,S-dioxide free base in ethyl acetate to afford a mixture;
(b) heating the mixture of step (a) to about 40° C. –60° C. to afford a solution;
(c) cooling the solution of step (b) to about 25° C. to afford solution A;
(d) dissolving oxalic acid in ethyl acetate to afford solution B;
(e) adding solution B to solution A at about 25° C. to form a precipitate comprising the anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide; and
(f) recovering the precipitate of step (e) to afford the anhydrous crystalline mono-oxalate salt of (RS)-7-(3-chloro-6-methyl-6,11-dihydrodibenzo[c,f] [1,2]thiazepin-11-ylamino)heptanoic acid S,S-dioxide.

20. The method of claim 16, wherein the psychiatric disorder induced by corticosteroid treatment is a trauma- and stressor-related disorder, a depressive disorder, a neurodegenerative disorder, or a neurodevelopmental disorder.

21. The method of claim 20, wherein the trauma- and stressor-related disorder is post-traumatic stress disorder (PTSD) or acute stress disorder (ASD); the depressive disorder is a major depressive disorder, a persistent depressive disorder, a bipolar depression, or a premenstrual dysphoric disorder; the neurodegenerative disorder is Alzheimer's disease or a multi-infarct dementia; or the neurodevelopmental disorder is an attention-deficit/hyperactivity disorder (ADHD).

* * * * *